US007754242B2

(12) United States Patent
Basu et al.

(10) Patent No.: US 7,754,242 B2
(45) Date of Patent: Jul. 13, 2010

(54) INHALABLE SUSTAINED THERAPEUTIC FORMULATIONS

(75) Inventors: Sujit K. Basu, Cambridge, MA (US);
Giovanni Caponetti, Piacenza (IT);
Robert Clarke, Canton, MA (US);
Katharina J. Elbert, Cambridge, MA (US)

(73) Assignee: Alkermes, Inc., Waltham, MA (US)

( * ) Notice: Subject to any disclaimer, the term of this patent is extended or adjusted under 35 U.S.C. 154(b) by 888 days.

(21) Appl. No.: 10/392,333

(22) Filed: Mar. 19, 2003

(65) Prior Publication Data
US 2004/0042970 A1     Mar. 4, 2004

Related U.S. Application Data

(60) Provisional application No. 60/366,479, filed on Mar. 20, 2002, provisional application No. 60/366,449, filed on Mar. 20, 2002, provisional application No. 60/366,354, filed on Mar. 20, 2002, provisional application No. 60/366,470, filed on Mar. 20, 2002, provisional application No. 60/366,487, filed on Mar. 20, 2002, provisional application No. 60/366,440, filed on Mar. 20, 2002.

(51) Int. Cl.
*A61K 9/16* (2006.01)
*A61K 9/12* (2006.01)
(52) U.S. Cl. .................. 424/489; 424/46; 424/498; 424/502
(58) Field of Classification Search ................ 424/489, 424/46, 498, 502
See application file for complete search history.

(56) References Cited

U.S. PATENT DOCUMENTS

| 4,780,476 A | * | 10/1988 | Grimminger et al. ........ 514/409 |
| 5,306,483 A | | 4/1994 | Mautone |
| 5,985,309 A | | 11/1999 | Edwards et al. |
| 5,997,848 A | | 12/1999 | Patton et al. |

(Continued)

FOREIGN PATENT DOCUMENTS

DE          199 21 693      * 11/2000

(Continued)

OTHER PUBLICATIONS

Peart, Joanne et al., "Multicomponent Particle Interactions in Dry Powder Aerosols," *Pharmaceutical Research*, 14(11 Suppl.) pp. S142-S143 (Nov. 1997).

*Primary Examiner*—Gollamudi S Kishore
(74) *Attorney, Agent, or Firm*—Elmore Patent Law Group, PC; Carolyn S. Elmore; Darlene A. Vanstone

(57) ABSTRACT

The present invention is based, in part, on the unexpected discovery that particles for pulmonary delivery of a therapeutic, prophylactic or diagnostic agent that comprise a phospholipid and a sufficient amount of leucine can produce sustained effect of the agent. Specifically, particles for pulmonary delivery of a therapeutic, prophylactic or diagnostic agent that contain a phospholipid or combination of phospholipids, wherein the phospholipid or combination of phospholipids is present in the particles in an amount of about 1 to 46 weight percent; and leucine, wherein leucine is present in the particles in an amount of at least 46 weight percent, can contribute to sustained effect of the agent. Particles that comprise at least 46 weight percent leucine but that do not contain phospholipids do not exhibit these same sustained effect properties.

22 Claims, 11 Drawing Sheets

Figure 1:
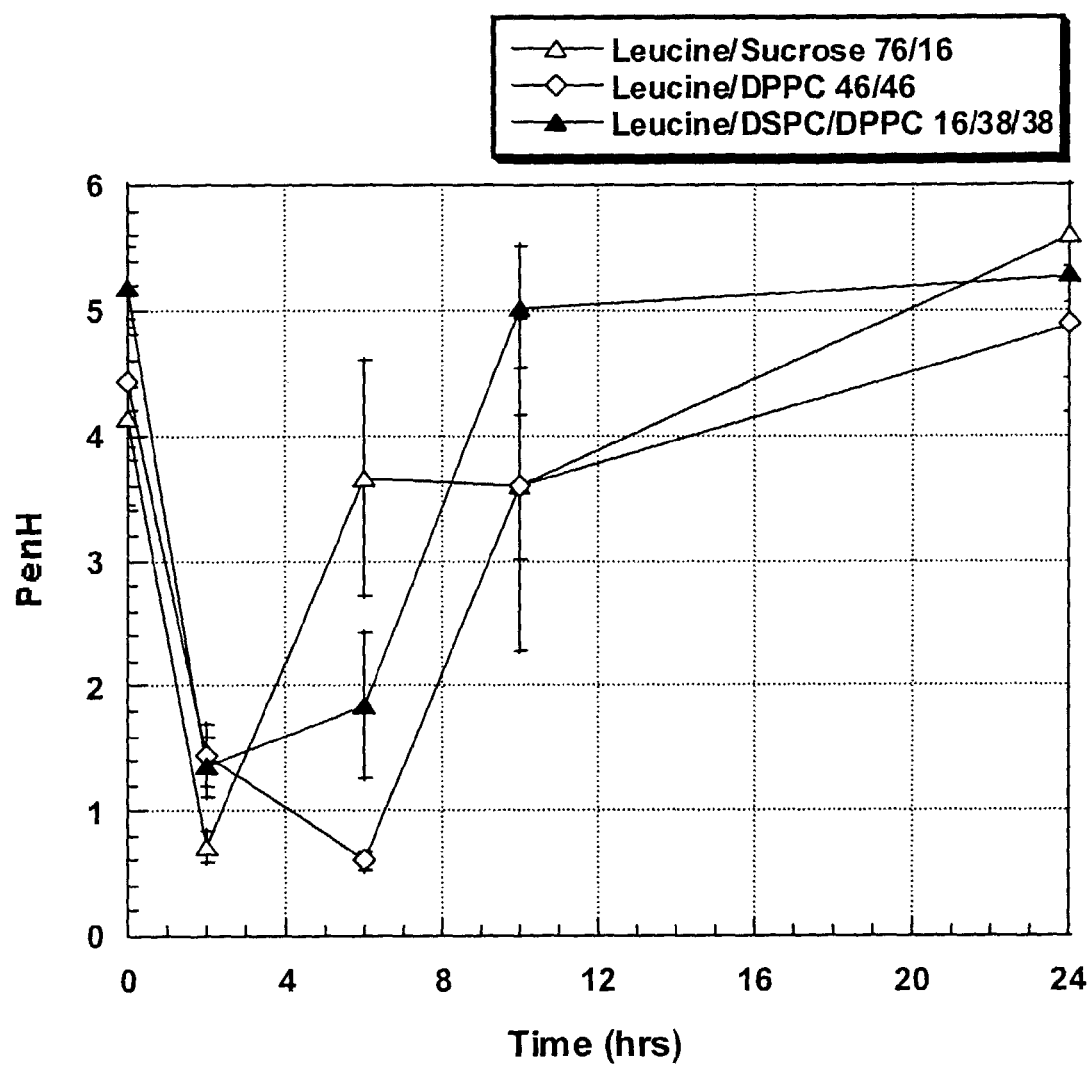

* = $P < 0.01$ Compared To Placebo Negative Control
α = $P < 0.01$ Compared To SX/Lac Positive Control
β = $P < 0.05$ Compared To SX/Lac Positive Control

U.S. PATENT DOCUMENTS

| | | | |
|---|---|---|---|
| 6,153,224 A | 11/2000 | Staniforth | |
| 6,284,287 B1 | 9/2001 | Sarlikiotis et al. | |
| 6,309,623 B1 * | 10/2001 | Weers et al. | 424/45 |
| 6,372,258 B1 | 4/2002 | Platz et al. | |
| 6,455,524 B1 | 9/2002 | Bozung et al. | |
| 6,586,008 B1 * | 7/2003 | Batycky et al. | 424/489 |

FOREIGN PATENT DOCUMENTS

| | | |
|---|---|---|
| WO | WO 96/23485 | 8/1996 |
| WO | WO 96/32096 | 10/1996 |
| WO | WO 00/33811 | 6/2000 |
| WO | 00/61178 A1 | 10/2000 |

* cited by examiner

INHALABLE SUSTAINED THERAPEUTIC FORMULATIONS

RELATED APPLICATIONS

This application claims the benefit of U.S. Provisional Application Nos. 60/366,479, 60/366,449, 60/366,354, 60/366,470, 60/366,487 and 60/366,440, all filed Mar. 20, 2002. This application is related to PCT Application entitled "Inhalable Sustained Therapeutic Formulations", PCT/US03/08537 being filed Mar. 19, 2003. The entire teachings of the above applications are incorporated herein by reference.

BACKGROUND OF THE INVENTION

Pulmonary delivery of therapeutic, diagnostic or prophylactic bioactive agents, provides an attractive alternative to other modes of administration such as, for example, oral, transdermal and parenteral administration. Typically, pulmonary administration can be completed without the need for medical intervention (i.e., self-administration is available), the pain often associated with injection therapy is avoided. In certain instances, the amount of enzymatic and pH mediated degradation of the bioactive agent, frequently encountered with oral therapies, can be significantly reduced. In addition, the lungs provide a large mucosal surface for drug absorption and there is no first-pass liver metabolism effect. Further, it has been shown that high bioavailability of many molecules, for example, macromolecules, can be achieved via pulmonary delivery. Typically, the deep lung, or alveoli, is the primary target of inhaled bioactive agents, particularly for agents requiring systemic delivery.

The release kinetics or release profile of a bioactive agent into the local and/or systemic circulation is a key consideration in most therapies, including those employing pulmonary delivery. Many illnesses or conditions require administration of a constant or sustained levels of a bioactive agent to provide an effective therapy. Typically, this can be accomplished through a multiple dosing regimen or by employing a system that releases the medicament in a sustained fashion.

However, delivery of bioactive agents to the pulmonary system typically results in rapid release of the agent following administration. For example, U.S. Pat. No. 5,997,848 to Patton, et al., describes the rapid absorption of insulin following administration of a dry powder formulation via pulmonary delivery. The peak insulin level was reached in about 30 minutes for primates and in about 20 minutes for human subjects. Further, Heinemann, Traut and Heise teach in Diabetic Medicine 14:63-72 (1997) that the onset of action of inhaled insulin, assessed by glucose infusion rate in healthy volunteers, was rapid with the half-maximal action reached in about 30 minutes.

As such, a need exists for formulations suitable for inhalation comprising bioactive agents and wherein the bioactive agent of the formulation is released in a sustained fashion into the systemic and/or local circulation.

Other aerosols for the delivery of therapeutic agents to the respiratory tract have been described, for example, Adjei, A. and Garren, *J. Pharm. Res.*, 7:565-569 (1990); and Zanen, P. and Lamm, J.-W. J., *Int. J. Pharm.*, 114:111-115 (1995). The respiratory tract encompasses the upper airways, including the oropharynx and larynx, followed by the lower airways, which include the trachea followed by bifurcations into the bronchi and bronchioli. The upper and lower airways are called the conducting airways. The terminal bronchioli then divide into respiratory bronchioli which then lead to the ultimate respiratory zone, the alveoli, or deep lung, as described in Gonda, I., "Aerosols for delivery of therapeutic and diagnostic agents to the respiratory tract," in *Critical Reviews in Therapeutic Drug Carrier Systems*, 6:273-313 (1990).

Inhaled aerosols have been used for the treatment of local lung disorders including asthma and cystic fibrosis (Anderson, *Am. Rev. Respir. Dis.*, 140:1317-1324 (1989)). Ipratropium bromide and salmeterol xinafoate are two agents that are currently prescribed for the treatment of lung disorders.

Ipratropium bromide is an anticholinergic bronchodilator chemically described as 8-azoniabi-cyclo (3.2.1)-octane, 3-(3-hydroxy-1-oxo-2-phenylpropoxy)-8-methyl-8-(1-methylethyl)-, bromide, monohydrate (endo,syn)-, (+/−)-, and is available commercially as Atrovent® Inhalation Aerosol (Boehringer Ingelheim). Atrovent is currently indicated as a bronchodilator for the maintenance treatment of bronchospasm associated with chronic obstructive pulmonary disease (COPD) including emphysema and chronic bronchitis.

The usual starting dose of Atrovent® is two inhalations (18 mcg of ipratropium bromide each inhalation) four times a day. Patients may take additional inhalations as needed, up to 12 inhalations in a day. Ninety day controlled studies in patients with bronchospasm associated with COPD showed improvement in pulmonary function (i.e., $\geq$15% improvement in $FEV_1$ and $FEF_{25-75\%}$) upon treatment with Atrovent® that began within 15 minutes, reached a peak in 1 to 2 hours, and persisted for 3 to 4 hours in the majority of patients and for up to 6 hours in some patients. (Physician's Desk Reference, 55th Ed. 962-963 (2001)).

Pulmonary function of a subject can be assessed as is commonly practiced by those experienced in the art. Forced Vital Capacity (FVC) is a measure of the maximum volume of air that a subject can expire after maximum inspiration. Forced expiratory volume in one second ($FEV_1$) is the volume of air that is expired in the first second of a FVC measurement. Forced expiratory flow 25-75% ($FEF_{25-75\%}$) is the average flowrate during the middle half of the forced expiratory maneuver of a FVC measurement.

Salmeterol is a long acting beta$_2$-adrenergic agonist bronchodilator chemically described as 4-hydroxy-a$^1$-[[[6-(4-phenylbutoxy)hexyl]amino]methyl]-1,3-benxenedimethanol, 1-hydroxy-2-napthalenecarboxylate (salmeterol xinafoate). Commercially, salmeterol xinafoate is available as Serevent® Inhalation Aerosol and as Serevent® Diskus® inhalation powder (GlaxoSmithKline). Serevent® Inhalation Aerosol is currently indicated for the maintenance treatment of asthma, for the prevention of bronchospasm in patients with reversible airway disease, and for the maintenance treatment of bronchospasm associated with chronic obstructive pulmonary disease (COPD) including emphysema and chronic bronchitis. Serevent® Diskus® is currently indicated for the maintenance treatment of asthma, for the prevention of bronchospasm in patients with reversible airway disease, and for the prevention of exercise induced bronchospasm.

The usual dosage for adults of Serevent® Inhalation Aerosol is 2 inhalations (21 mcg of salmeterol base each inhalation) twice daily (approximately 12 hours apart). The usual dosage for adults of Serevent® Diskus® is one inhalation (50 mcg of salmeterol) twice daily (approximately 12 hours apart). Clinical trials showed the time to onset of effective bronchodilation (i.e., $\geq$15% improvement in $FEV_1$) was 10 to 20 minutes following administration of Serevent® Inhalation Aerosol. The median time to onset of effective bronchodilation (i.e., $\geq$15% improvement in $FEV_1$) was 30 to 48 minutes following administration of a 50 mcg dose of Serevent® Diskus®. Both formulations showed maximum improvement in $FEV_1$ (forced expiratory volume in one second) generally occurring within 180 minutes and clinically significant improvement continuing for 12 hours in most patients. (Physician's Desk Reference, 55$^{th}$ Ed. 1464-1471 (2001)).

A long-term study of the combination of salmeterol and ipratropium in patients with stable chronic obstructive pulmonary disease (COPD) found that when compared to salmeterol alone, the combination of salmeterol with ipratropium showed the greatest improvement in forced expiratory volume in one second ($FEV_1$) and specific airway conductance (Van Noord, et al., Eur Respir J 2000; 15:878). All medications were inhaled from a metered dose inhaler (MDI) attached to a Volumatic® aerosol chamber (GlaxoWellcome, United Kingdom).

WO 01/76601 discloses formulations combining micronized salmeterol and ipratropium bulk blended with lactose. The blended powder is to be administered by Rotahaler, Diskhaler, or Diskus Inhaler (each a trademark of GlaxoGroup Ltd.).

However, pulmonary drug delivery strategies such as those described above, possess many limitations including excessive loss of inhaled drug in the oropharyngeal cavity (often exceeding 80%), poor control over the site of deposition, lack of reproducibility of therapeutic results owing to variations in breathing patterns, frequent too-rapid absorption of drug potentially resulting in local toxic effects, and potential for rapid elimination via phagocytosis by lung macrophages.

There exists a need for a dry powder pharmaceutical composition, especially one with a more homogenous particle size distribution and capable of being delivered without further blending, for pulmonary delivery of salmeterol and ipratropium. Furthermore, there exists a need for a dry powder pharmaceutical composition comprising salmeterol and ipratropium that allows for simplified and efficient delivery to the pulmonary system such as once or twice per day administration. There also exists a need for dry powder pharmaceutical compositions comprising salmeterol and ipratropium that are able to withstand the environmental stresses of everyday activities while still maintaining desirable physical and chemical stability as well as desirable duration of action.

SUMMARY OF THE INVENTION

The present invention is based, in part, on the unexpected discovery that particles for pulmonary delivery of a therapeutic, prophylactic or diagnostic agent that comprise a phospholipid and a sufficient amount of leucine can produce sustained effect of the agent. Specifically, particles for pulmonary delivery of a therapeutic, prophylactic or diagnostic agent comprising a phospholipid or combination of phospholipids, wherein the phospholipid or combination of phospholipids is present in the particles in an amount of about 1 to 46 weight percent; and leucine, wherein leucine is present in the particles in an amount of at least 46 weight percent, can contribute to sustained effect of the agent. Particles that comprise at least 46 weight percent leucine but that do not contain phospholipids do not exhibit these same sustained effect properties. In one aspect the invention is directed toward particles for drug delivery and methods for delivering the particles to the pulmonary system. The particles and respirable compositions comprising the particles of the present invention described herein comprise ipratropium bromide and salmeterol xinafoate as therapeutic agents. The terms "salmeterol" and "salmeterol xinafoate" are used interchangeably herein. The terms "ipratropium" and "ipratropium bromide" are used interchangeably herein.

Applicant's claimed invention is directed toward non-polymeric particles for pulmonary delivery of a therapeutic, prophylactic or diagnostic agent and methods for delivery of a therapeutic, prophylactic or diagnostic agent to the pulmonary system. In one aspect, the present invention relates to particles comprising a therapeutic, prophylactic or diagnostic agent; a phospholipid or combination of phospholipids, wherein the phospholipid or combination of phospholipids is present in the particles in an amount of from about 1 to about 46 weight percent; and leucine, wherein leucine is present in the particles in an amount of at least 46 weight percent. In another aspect of the present invention, non-polymeric particles are capable of extending the duration release of the agent from the particle.

The particles of the present invention are preferably "aerodynamically light". As described herein, "aerodynamically light" refers to particles having a tap density of less than 0.4 g/cm$^3$. In one embodiment, the particles have a tap density of less than about 0.25 g/cm$^3$. The particles of the invention have a preferred size, e.g., a volume median geometric diameter (VMGD) of at least about 1 micron (μm). In one embodiment, the VMGD is from about 1 μm to 30 μm, or any subrange encompassed by about 1 μm to 30 μm, for example, but not limited to, from about 5 μm to about 30 μm, or from about 10 μm to 30 μm. For example, the particles have a VMGD ranging from about 1 μm to 10 μm, or from about 3 μm to 7 μm, or from about 5 μm to 15 μm or from about 9 μm to about 30 μm. The particles have a median diameter, mass median diameter (MMD), a mass median envelope diameter (MMED) or a mass median geometric diameter (MMGD) of at least 1 μm, for example, 5 μm or near to or greater than about 10 μm. For example, the particles have a MMGD greater than about 1 μm and ranging to about 30 μm, or any subrange encompassed by about 1 μm to 30 μm, for example, but not limited to, from about 5 μm to 30 μm or from about 10 μm to about 30 μm. In yet another embodiment, the particles of the invention have an aerodynamic diameter of about 1 to 5 microns.

In one aspect, the present invention is directed to a method for pulmonary delivery of a therapeutic, prophylactic or diagnostic agent.

The method comprises administering or co-administering to the respiratory tract of a patient in need of treatment, prophylaxis or diagnosis an effective amount of non-polymeric particles comprising a therapeutic, prophylactic or diagnostic agent, including combinations of agents; a phospholipid or combination of phospholipids, wherein the phospholipid or combination of phospholipids is present in the particles in an amount of about 1 to 46 weight percent; and leucine, wherein leucine is present in the particles in an amount of at least 46 weight percent, and wherein the particles have a tap density of less than about 0.4 g/cm3.

One objective of the present invention is to create dry powder pharmaceutical compositions capable of delivering effective quantities of bioactive agents to the pulmonary system of a subject in need of treatment, prophylaxis or diagnosis.

Another objective is to simplify the manufacture of a combination drug product containing bioactive agents.

Another objective is to optimize the quantity of bioactive agents that must be delivered to the pulmonary system to achieve effective treatment, prophylaxis or diagnosis.

Another objective is to provide effective therapy to a patient in need of bioactive agents while minimizing the occurrence of undesired side effects.

Another objective of the present invention is to provide a mechanism for delivering a bioactive agent or multiple bioactive agents to the same local site in the lungs.

Another objective is to improve treatment options for subjects in need of bioactive agents, for example, by reducing frequency of dosing or by extending the duration of action of either or both agents.

Yet another objective of the present invention is to create dry powder pharmaceutical compositions comprising bioactive agents capable of withstanding the environmental stresses, such as thermal stress, of everyday activities.

BRIEF DESCRIPTION OF THE DRAWINGS

The foregoing and other objects, features and advantages of the invention will be apparent from the following more particular description of preferred embodiments of the invention.

FIG. 1 is a plot showing enhanced pause (PenH) versus time, in hours, for bronchoprotection provided by three particle formulations comprising albuterol in a guinea pig model of airway hyperresponsiveness.

FIG. 2 is a plot of blood plasma albuterol concentration, in ng albuterol/mL, versus time, in hours, for an in vivo pharmacokinetic study of three particle formulations in Sprague-Dawley rats.

FIG. 3 is a plot demonstrating the influence of composition comprising albuterol on the reduction of particle mass mean diameter, as a percent reduction of initial size, over time, in minutes, under fully hydrated conditions.

FIG. 4 is a dynamic vapor sorption (DVS) moisture sorption isotherm for particles containing DPPC, DSPC, leucine, ipratropium bromide and salmeterol xinafoate (Formulation A from Table I through IX).

FIG. 5 is a DVS moisture sorption isotherm for particles containing DPPC, DSPG, leucine, ipratropium bromide and salmeterol xinafoate (Formulation B from Table I through IX).

FIG. 6 is a DVS moisture sorption isotherm for particles containing leucine, ipratropium bromide, and salmeterol xinafoate (Formulation C from Table I through IX).

FIG. 7 is a DVS moisture sorption isotherm for particles containing leucine, mannitol, ipratropium bromide and salmeterol xinafoate (Formulation D from Table I through IX).

FIG. 8 is a DVS moisture sorption isotherm for particles containing MSPC, DMPE, leucine, ipratropium bromide and salmeterol xinafoate (Formulation E from Table I through IX).

FIG. 9 is a chart summarizing a 12 hour study of bronchoprotection in a guinea pig model of airway hyperresponsiveness for ten particle formulations (Formulations A, B, C, D, E, F, H, I, J, K from Tables I and III), salmeterol/lactose and placebo.

FIG. 10 is a graph of enhanced pause (PenH) versus time, in hours, for a multipoint study of bronchoprotection in a guinea pig model of airway hyperresponsiveness for five particle formulations (Formulations A, B, C, D, E from Table I) and salmeterol/lactose (SXLac).

FIG. 11 is a graph of percent of baseline enhanced pause versus time, in hours, for a multipoint study of bronchoprotection in a guinea pig model of airway hyperresponsiveness for five particle formulations (Formulations A, B, C, D, E from Table I) and salmeterol/lactose (SXLac).

DETAILED DESCRIPTION OF THE INVENTION

A description of preferred embodiments of the invention follows.

The present invention is directed toward particles for drug delivery and methods for delivering the particles comprising therapeutic, prophylactic or diagnostic agent or agents to the pulmonary system. The present invention is based, in part, on the unexpected discovery that particles for pulmonary delivery of a therapeutic, prophylactic or diagnostic agent that comprise a phospholipid and a sufficient amount of leucine can produce sustained effect of the agent.

Suitable agents are corticosteroids including, but not limited to beclomethasome, budesonide, ciclesonide, flunisolide, fluticasone, mometasome, rofleponide, triamcinalone, salmeterol, salmeterol xinofoate, terbutaline; beta-2 agonists including, but not limited to albuterol, bitolterol, fenoterol, formoterol, isoetharine, isoproterenol, metaproterenol, pirbuterol; anticholinergics including, but not limited to ipratropium bromide, tiatropium, Ba679BR, trospium.

Further, combinations of any one class with any other class (or one from all three classes) are suitable for treatment of asthma and/or COPD. These combinations are combinations of beta-2 agonists and corticosteroids including, but not limited to salmeterol and beclometasome, salmeterol and fluticasone, salmeterol and budesonide, salmeterol and mometasome, salmeterol and rofleponide, formoterol and budesonide, formoterol and fluticasone, formoterol and mometasome, formoterol and rofleponide, formoterol and beclomethasome; combinations of beta-2 and anticholinergic including, but not limted to albuterol and ipratropium bromide, salmeterol and ipratropium bromide, formoterol and tiatropium, fenoterol and ipratropium bromide, albuterol and trospium, bitolterol and trospium, fenoterol and trospium, formoterol and trospium, isoetharine and trospium, isoproterenol and trospium, metaproterenol and trospium, pirbuterol and trospium; and combinations of corticosteroid and anticholinergic, including, but not limted to budesonide and tiatropium, fluticasone and tiatropium, mometasome and tiatropium, rofleponide and tiatropium, beclomethasome and trospium, budesonide and trospium, ciclesonide and trospium, flunisolide and trospium, fluticasone and trospium, mometasome and trospium, rofleponide and trospium, triamcinalone and trospium, salmeterol and trospium, terbutaline and trospium.

It will be understood by one skilled in the art that pharmaceutically acceptable salts of the above agents are suitable in the practice of the invention. As used herein, a "pharmaceutically acceptable salt" of the disclosed compound is an ionic bond-containing product of reacting a compound of the invention with either an acid or a base, suitable for administering to a subject. For example, an acid salt of a compound containing an amine or other basic group can be obtained by reacting the compound with a suitable organic or inorganic acid, such as hydrogen chloride, hydrogen bromide, acetic acid, perchloric acid and the like. Compounds with a quaternary ammonium group also contain a counteranion such as chloride, bromide, iodide, acetate, perchlorate and the like. Other examples of such salts include hydrochlorides, hydrobromides, sulfates, methanesulfonates, nitrates, maleates, acetates, citrates, fumarates, tartrates (e.g. (+)-tartrates, (−)-tartrates or mixtures thereof including racemic mixtures), succinates, benzoates and salts with amino acids such as glutamic acid. Salts can also be formed with suitable organic bases when the compound comprises an acid functional group such as —COOH or —$SO_3H$. Such bases suitable for the formation of a pharmaceutically acceptable base addition salts with compounds of the present invention include organic bases that are nontoxic and strong enough to form salts. Such organic bases are well known in the art and may include amino acids such as arginine and lysine, mono-, di-, and triethanolamine, choline, mono-, di-, and trialkylamine, such as methylamine, dimethylamine, and trimethylamine, guanidine, N-benzylphenethylamine; N-methylglucosamine; N-methylpiperazine; morpholine; ethylendiamine; tris(hydroxymethyl)aminomethane; and the like.

The particles and respirable compositions comprising the particles of the invention, both hereinafter referred to as "particles" or "powders," are also preferably biodegradable and biocompatible, and optionally are capable of affecting the biodegradability and/or the rate of delivery of the co-administered agents. In addition to an agent, preferably a bioactive agent, the particles can further include a variety of materials. Both inorganic and organic materials can be used. Suitable materials can include, but are not limited to, lipids, fatty acids, inorganic salts, amino acids, polyethylene glycol, precirol, trehalose, mannitol, lactose, and maltodextrin. Preferred particle compositions are further described below.

The present invention has numerous advantages. For example, practice of the present invention permits pulmonary delivery of a single dose of particles that comprises therapeutic, prophylactic or diagnostic agent or agents to a patient in need of treatment, prophylaxis or diagnosis.

The present invention is directed to pulmonary delivery of a therapeutic, prophylactic or diagnostic agent. Applicant's claimed invention is directed toward non-polymeric particles for pulmonary delivery of a therapeutic, prophylactic or diagnostic agent and methods for delivery of a therapeutic, prophylactic or diagnostic agent to the pulmonary system comprising administering to the respiratory tract of a patient an effective amount of particles, which comprise a therapeutic, prophylactic or diagnostic agent; a phospholipid or combination of phospholipids, wherein the phospholipid or combination of phospholipids is present in the particles in an amount of about 1 to 46 weight percent; and leucine, wherein leucine is present in the particles in an amount of at least 46 weight percent, and which have sustained drug release kinetics and/or therapeutic action. In one embodiment, the particles are in the form of a dry powder suitable for inhalation.

In one embodiment, an effective amount of therapeutic, prophylactic or diagnostic agent or agents is administered to the pulmonary system, for example, via a dry powder inhaler (DPI), with high efficiency. Use of a DPI with the powder formulations disclosed herein increases efficiency, minimizes wasted drug, and decreases overall cost. Since dose frequency may be reduced by the delivery method that dry powder makes possible, patient compliance to treatment protocols is expected to improve. Furthermore, enhancing properties of the particles themselves can result in a dose advantage, where the desired effect is achieved with a reduced amount of therapeutic, prophylactic or diagnostic agent or agents. In another embodiment, an effective amount is administered by a dry powder inhaler (DPI), for example, a Rotahaler, Diskhaler or Diskus Inhaler, in which a single dose comprises either a single receptacle such as a capsule or blister, or a dose comprises more than one receptacle.

The present invention is also directed to particles suitable for inhalation therapy wherein a therapeutic, prophylactic or diagnostic agent for systemic or local action is released in a sustained fashion. Further, the invention also is directed to particle formulations wherein an agent is released from the particles in a controlled manner. For example, the particles can be designed to possess a sustained release profile. This sustained released profile can provide for prolonged residence of one or more of the administered agent(s) in the lung and increase the amount of time in which therapeutic levels of one or more of the agents are present in the local environment or systemic circulation.

In a preferred embodiment, the particles possess aerosol characteristics that permit effective delivery of the particles to the respiratory system without the use of propellents. For example, particles may be evaluated for aerosol performance based on such characteristics as geometric diameter, aerodynamic diameter, tap density, and fine particle fraction.

The diameter of the particles, for example, their VMGD, can be measured using an electrical zone sensing instrument such as a Multisizer IIe, (Coulter Electronic, Luton, Beds, England), or a laser diffraction instrument such as HELOS (Sympatec, Princeton, N.J.). Other instruments for measuring particle geometric diameter are well known in the art. The diameter of particles in a sample will range depending upon factors such as particle composition and methods of synthesis. The distribution of size of particles in a sample can be selected to permit optimal deposition within targeted sites within the respiratory tract.

Particles suitable for use in the present invention may be fabricated or separated, for example by filtration or centrifugation, to provide a particle sample with a preselected size distribution. For example, greater than about 30, 50, 70, or 80% of the particles in a sample can have a diameter of at least about 1 microns, for example about 5 microns. The selected range within which a certain percentage of the particles must fall may be about 1 μm to 30 μm, or any subrange encompassed by about 1 μm to 30 μm, for example, but not limited to between about 5 and 30 microns or optionally between about 5 and 15 microns. Optionally, the particle sample also can be fabricated wherein at least about 90% or optionally about 95 or 99% of the particles, have a diameter within the selected range. An interquartile range of the particle sample may be 2 microns, with a mean diameter for example, between about 7.5 and 13.5 microns. Thus, for example, at least about 30 to 40% of the particles may have diameters within the selected range. Preferably, the said percentages of particles have diameters within a 1 micron range, for example, between 6 and 7; 10 and 11; 13 and 14; or 14 and 15 microns.

In one embodiment, particles of the present invention are capable of releasing an agent in a sustained fashion. As such, the particles can be said to possess sustained release properties. "Sustained release" as that term is used herein, refers to an increase in the time period over which an agent is released from a particle of the present invention as compared to an appropriate control, such as for example, as compared to the time period over which an agent is released from an particle that does not comprise a therapeutic, prophylactic or diagnostic agent; a phospholipid or combination of phospholipids, wherein the phospholipid or combination of phospholipids is present in the particles in an amount of about 1 to 46 weight percent; and leucine, wherein leucine is present in the particles in an amount of at least 46 weight percent. For example, a sustained release of albuterol from the particles of the present invention can be a release showing in vivo bronchoprotection out to at least 4 hours post administration, such as about 5 to 6 hours or more. "Sustained release," as that term is used herein, may also refer to a reduction in the availability, or burst, of agent typically seen soon after administration. For example, "sustained release" can refer to a reduction in the availability of an agent in the first hour following administration, often referred to as the high initial release or burst. By controlling the burst, patient compliance and comfort can be increased by not only reducing the frequency of dosing, but also by providing a therapy which is more amenable to patients.

"Sustained release," as that term is used herein, may also refer to a higher amount of drug retained or remaining in the particles after the initial burst as compared to an appropriate control. "Sustained release" is also known to those experienced in the art as "modified release," "prolonged release," or "extended release." "Sustained-release," as used herein, also encompasses "sustained action" or "sustained effect." "Sustained action" and "sustained effect," as those terms are used herein, can refer to an increase in the time period over which an agent performs its therapeutic, prophylactic or diagnostic activity as compared to an appropriate control. "Sustained action" is also known to those experienced in the art as "prolonged action" or "extended action."

Without being held to any particular theory, Applicants believe that the sustained effect provided by particles of the instant invention may be, among other factors, influenced by the rate of drug release from the particles. Drug release rates can be described in terms of the half-time of release of a bioactive agent from a formulation. As used herein the term "half-time" refers to the time required to release 50% of the initial drug payload contained in the particles. In one embodiment, the particles of the present invention have a half-time of release of an agent from the particles of greater than about 1 hour.

Drug release rates can also be described in terms of release constants. The first order release constant can be expressed using one of the following equations:

$$Mpw(t)=M(\infty)*(e^{-k*t}) \quad (1)$$

or, $$M(t)=M(\infty)*(1-e^{-k*t}) \quad (2)$$

Where k is the first order release constant. M ($\infty$) is the total mass of drug in the drug delivery system, e.g. the dry powder, and M pw (t) is drug mass remaining in the dry powders at time t. M (t) is the amount of drug mass released from dry powders at time t. The relationship can be expressed as:

$$M(\infty)=Mpw(t)+M(t) \quad (3)$$

Equations (1), (2) and (3) may be expressed either in amount (i.e., mass) of drug released or concentration of drug released in a specified volume of release medium.

For example, Equation (2) may be expressed as:

$$C(t)=C(\infty)*(1-e^{-k*t}) \quad (4)$$

Where k is the first order release constant. C ($\infty$) is the maximum theoretical concentration of drug in the release medium, and C (t) is the concentration of drug being released from dry powders to the release medium at time t.

The 'half-time' or $t_{50\%}$ for a first order release kinetics is given by the well-known equation, $$t_{50\%}=0.693/k \quad (5)$$

Drug release rates in terms of first order release constant and t50% may be calculated using the following equations:

$$k=-\ln(Mpw(t)/M(\infty))/t \quad (6)$$

or, $$k=-\ln(M(\infty)-M(t))/M(\infty)/t \quad (7)$$

In a preferred embodiment, the particles of the invention have extended drug release properties in comparison to the pharmacokinetic/pharmacodynamic profile of the drug administered alone or in conventional formulations, such as by the intravenous route.

Furthermore, it was also discovered, unexpectedly, that particles comprising a therapeutic, prophylactic or diagnostic agent; a phospholipid or combination of phospholipids, wherein the phospholipid or combination of phospholipids is present in the particles in an amount of about 1 to 46 weight percent; and leucine, wherein leucine is present in the particles in an amount of at least 46 weight percent, exhibit desirable controlled and gradual reduction of their size over time, when dispersed in isotone solution at 37° C. The phospholipid or combination of phospholipids can be present in the particles in an amount ranging from about 1 to 46 weight percent. More commonly, the phospholipid or combination of phospholipids can be present in the particles in an amount ranging from about 10 to 46 weight percent.

The particles of the present invention comprise a therapeutic, prophylactic or diagnostic agent, also referred to herein as "bioactive agents," "agents," "medicaments," or "drugs." Therapeutic, prophylactic or diagnostic agents or combinations thereof can be employed. Hydrophilic as well as hydrophobic drugs can be used. Optionally, agents may be present in the particles in the form of a salt.

Suitable bioactive agents include both locally as well as systemically acting drugs. Examples include but are not limited to synthetic inorganic and organic compounds, proteins and peptides, polysaccharides and other sugars, lipids, and DNA and RNA nucleic acid sequences having therapeutic, prophylactic or diagnostic activities. Nucleic acid sequences include genes, antisense molecules which can, for instance, bind to complementary DNA to inhibit transcription, and ribozymes. The agents can have a variety of biological activities, such as vasoactive agents, neuroactive agents, hormones, anticoagulants, immunomodulating agents, cytotoxic agents, prophylactic agents, antibiotics, antivirals, antisense, antigens, antineoplastic agents and antibodies. In some instances, the proteins may be antibodies or antigens which otherwise would have to be-administered by injection to elicit an appropriate response. Compounds with a wide range of molecular weight can be used, for example, compounds having a mass between 100 and 500,000 grams or more per mole. Proteins are defined as consisting of 100 amino acid residues or more; peptides are less than 100 amino acid residues. Unless otherwise stated, the term "protein" refers to both proteins and peptides. Examples include insulin, other hormones and antibodies. Polysaccharides, such as heparin, can also be administered.

The particles may include a bioactive agent for local delivery within the lung, such as agents for the treatment of asthma, chronic obstructive pulmonary disease (COPD), emphysema, or cystic fibrosis, or for systemic treatment. For example, genes for the treatment of diseases such as cystic fibrosis can be administered, as can beta agonists, steroids, anticholinergics, and leukotriene modifers for asthma. Other specific therapeutic agents include, but are not limited to, insulin, calcitonin, luteinizing hormone releasing hormone ("LHRH"), or gonadotropin-releasing hormone, granulocyte colony-stimulating factor ("G-CSF"), parathyroid hormone-related peptide, somatostatin, testosterone, progesterone, estradiol, nicotine, fentanyl, norethisterone, clonidine, scopolomine, salicylate, cromolyn sodium, salmeterol, formeterol, estrone sulfate, and diazepam.

Those therapeutic agents which are charged, such as most of the proteins, including insulin, can be administered as a complex between the charged therapeutic agent and a molecule of opposite charge. Preferably, the molecule of opposite charge is a charged lipid or an oppositely charged protein.

The particles can include any of a variety of diagnostic agents to locally or systemically deliver the agents following administration to a patient. Any biocompatible or pharmacologically acceptable gas can be incorporated into the particles or trapped in the pores of the particles using technology known to those skilled in the art. The term gas refers to any compound which is a gas or capable of forming a gas at the temperature at which imaging is being performed. In one embodiment, retention of gas in the particles is improved by forming a gas-impermeable barrier around the particles. Such barriers are well known to those of skill in the art.

Other imaging agents which may be utilized include commercially available agents used in positron emission tomography (PET), computer assisted tomography (CAT), single photon emission computerized tomography, x-ray, fluoroscopy, and magnetic resonance imaging (MRI).

Examples of suitable materials for use as contrast agents in MRI include the gadolinium chelates currently available, such as diethylene triamine pentacetic acid (DTPA) and gadopentotate dimeglumine, as well as iron, magnesium, manganese, copper, chromium, technecium, europium, and other radioactive imaging agents.

Examples of materials useful for CAT and x-rays include iodine based materials for intravenous administration, such as ionic monomers typified by diatrizoate and iothalamate, non-ionic monomers such as iopamidol, isohexol, and ioversol, non-ionic dimers, such as iotrol and iodixanol, and ionic dimers, for example, ioxagalte. Diagnostic agents can be detected using standard techniques available in the art and commercially available equipment.

The amount of therapeutic, prophylactic or diagnostic agent(s) present in the particles can range from about 0.1 to 40 weight percent. Combinations of agents also can be present in the particles. In one embodiment, the amount of therapeutic, prophylactic or diagnostic agent(s) present in the particles is about 1 to 25 weight percent, such as about 5 to 15 weight percent. In another embodiment, the amount of therapeutic, prophylactic or diagnostic agent(s) present in the particles is about 5 to 10 weight percent, for example, about 8 weight percent.

The particles and respirable compositions comprising the particles of the invention comprise a phospholipid or a combination of phospholipids. Examples of suitable phospholipids include, among others, those listed and described in U.S. patent application Ser. No. 09/792,869 entitled "Modulation of Release From Dry Powder Formulations", filed on Feb. 23, 2001, which is a Continuation-in-part of U.S. patent application Ser. No. 09/644,736, entitled "Modulation Of Release From Dry Powder Formulations", filed on Aug. 23, 2000, which is a Continuation-in-part of U.S. Patent Application No. 60/150,742 entitled "Modulation of Release From Dry Powder Formulations by Controlling Matrix Transition," filed on Aug. 25, 1999. The contents of these applications are incorporated by reference in their entirety. Other suitable phospholipids include phosphatidylcholines, phosphatidylethanolamines, phosphatidylglycerols, phosphatidylserines, phosphatidylinositols and combinations thereof. Specific examples of phospholipids include but are not limited to 1,2-dipalmitoyl-sn-glycero-3-phosphocholine (DPPC), 1,2-distearoyl-sn-glycero-3-phosphocholine (DSPC), 1-myristoyl, -2-stearoyl-sn-glycero-3-phosphocholine (MSPC), 1,2-dimyristoyl-sn-glycero-3-phosphoethanolamine (DMPE), 1,2-distearoyl-sn-glycero-3-[phospho-rac-(1-glycerol)] (DSPG), 1,2-dipalmitoyl-sn-glycero-3-phosphoethanolamine (DPPE), or any combination thereof. Other phospholipids are known to those skilled in the art. In a preferred embodiment, the phospholipids are endogenous to the lung.

The phospholipid or combination of phospholipids can be present in the particles in an amount ranging from about 1 to 46 weight percent. More commonly, the phospholipid or combination of phospholipids can be present in the particles in an amount ranging from about 10 to 46 weight percent. In one embodiment, the total phospholipid content is about 35 to 46 weight percent. In another embodiment, the total phospholipid content is about 46 weight percent. In yet another embodiment, the total phospholipid content can be present in the particles in an amount ranging from about 10 to 60 weight percent In another embodiment of the invention, the phospholipids or combinations thereof are selected to impart controlled release properties to the highly dispersible particles. The phase transition temperature of a specific phospholipid can be below, around, or above the physiological body temperature of a patient. By selecting phospholipids or combinations of phospholipids according to their phase transition temperature, the particles can be tailored to have controlled release properties. For example, by administering particles which include a phospholipid or combination of phospholipids which have a phase transition temperature higher than the patient's body temperature, the release of an agent, such as albuterol, can be slowed down. On the other hand, rapid release can be obtained by including in the particles phospholipids having lower transition temperatures.

Particles having controlled release properties and methods of modulating release of a biologically active agent are described in U.S. patent application Ser. No. 09/792,869 entitled "Modulation of Release From Dry Powder Formulations", filed on Feb. 23, 2001, which is a Continuation-in-part of U.S. patent application Ser. No. 09/644,736, entitled "Modulation Of Release From Dry Powder Formulations", filed on Aug. 23, 2000, which is a Continuation-in-part of U.S. Patent Application No. 60/150,742 entitled "Modulation of Release From Dry Powder Formulations by Controlling Matrix Transition," filed on Aug. 25, 1999. The contents of these applications are incorporated by reference in their entirety.

Particle aerodynamic diameter can also be used to characterize the aerosol performance of a composition. In one embodiment, the particles have a mass median aerodynamic diameter (MMAD) of about 1 to 5 microns. In another embodiment, the particles have a MMAD of about 1 to 3 microns. In another aspect, have a MMAD of about 2 to 4 microns. In yet another embodiment, the particles have a MMAD of about 3 to 5 microns.

Experimentally, aerodynamic diameter can be determined using time of flight (TOF) measurements. For example, an instrument such as the Model 3225 Aerosizer DSP Particle Size Analyzer (Amherst Process Instrument, Inc., Amherst, Mass.) can be used to measure aerodynamic diameter. The Aerosizer measures the time taken for individual particles to pass between two fixed laser beams. The instrument subsequently uses this TOF data to solve a force balance on the particles and aerodynamic diameter is determined based on the relationship $$d_{aer} \propto d\sqrt{r}$$

where $d_{aer}$ is the aerodynamic diameter of the particle; d is the diameter of the particle; and r is the particle density.

Aerodynamic diameter also can be experimentally determined by employing a gravitational settling method, whereby the time for an ensemble of particles to settle a certain distance is used to infer directly the aerodynamic diameter of the particles. Indirect methods for measuring the mass median aerodynamic diameter are the Andersen Cascade Impactor and the multi-stage liquid impinger (MSLI). The methods and instruments for measuring particle aerodynamic diameter are well known in the art.

Fine particle fraction can be used as one way to characterize the aerosol performance of a dispersed powder. Fine particle fraction describes the size distribution of airborne particles. Gravimetric analysis, using cascade impactors, is one method of measuring the size distribution, or fine particle fraction, of airborne particles. The Andersen Cascade Impactor (ACI) is an eight-stage impactor that can separate aerosols into nine distinct fractions based on aerodynamic size. The size cutoffs of each stage are dependent upon the flow rate at which the ACI is operated.

In one embodiment, a two-stage collapsed ACI also is used to measure fine particle fraction. The two-stage collapsed ACI consists of only the top two stages of the eight-stage ACI and allows for the collection of two separate powder fractions. The ACI is made up of multiple stages consisting of a series of nozzles and an impaction surface. At each stage an aerosol stream passes through the nozzles and impinges upon the surface. Particles in the aerosol stream with a large enough inertia will impact upon the plate. Smaller particles that do not have enough inertia to impact on the plate will remain in the aerosol stream and be carried to the next stage. Each successive stage of the ACI has a higher aerosol velocity in the nozzles so that smaller particles can be collected at each successive stage.

In one embodiment, the particles of the invention are characterized by fine particle fraction. A two-stage collapsed Andersen Cascade Impactor is used to determine fine particle fraction. Specifically, a two-stage collapsed ACI is calibrated so that the fraction of powder that is collected on stage one is composed of particles that have an aerodynamic diameter of less than 5.6 microns and greater than 3.4 microns. The fraction of powder passing stage one and depositing on a collection filter is thus composed of particles having an aerodynamic diameter of less than 3.4 microns. The airflow at such a calibration is approximately 60 L/min.

The terms "FPF(<5.6) and "fine particle fraction, less than 5.6 microns," as used herein, refer to the fraction of a sample of particles that have an aerodynamic diameter of less than 5.6 microns. FPF(<5.6) can be determined by dividing the mass of particles deposited on the stage one and on the collection filter of a two-stage collapsed ACI by the mass of particles weighed into a capsule for delivery to the instrument.

The terms "FPF (<3.4)" and "fine particle fraction, less than 3.4 microns," as used herein, refer to the fraction of a mass of particles that have an aerodynamic diameter of less than 3.4 microns. FPF(<3.4) can be determined by dividing the mass of particles deposited on the collection filter of a two-stage collapsed ACI by the mass of particles weighed into a capsule for delivery to the instrument.

The FPF(<5.6) has been demonstrated to correlate to the fraction of the powder that is able to make it into the lungs of the patient, while the FPF(<3.4) has been demonstrated to correlate to the fraction of the powder that reaches the deep lung of a patient. These correlations provide a quantitative indicator that can be used for particle optimization.

Multi-stage liquid Impinger (MSLI) is another device that can be used to measure fine particle fraction. The MSLI operates on the same principles as the Anderson Cascade Impactor, although instead of eight stages, the MSLI has five. Additionally, as used in one embodiment, each MSLI stage consists of an ethanol-wetted glass frit instead of a solid plate. The wetted stage is used to prevent particle bounce and re-entrainment, which can occur using the ACI.

In one embodiment, a mass of particles of the invention has a FPF(<5.6) of at least about 40%. In a preferred embodiment, a mass of particles of the invention has a FPF(<5.6) of greater than about 50%. Even more preferred, a mass of particles has a FPF(<5.6) of greater than about 60%. In another embodiment, the particles have a FPF (<3.4) of greater than about 10%, for example, a FPF (<3.4) greater than about 20%.

In one embodiment of the invention, particles administered to a subject's respiratory tract have a tap density of less than about 0.4 g/cm$^3$. Particles having a tap density of less than about 0.4 g/cm$^3$ are referred to herein as "aerodynamically light". In another embodiment, the particles have a tap density less than about 0.3 g/cM$^3$, less than about 0.25 g/cm$^3$, or less than about 0.2 g/cm$^3$. In yet another embodiment, the particles have a tap density less than about 0.1 g/cm$^3$. Tap density is a measure of the envelope mass density characterizing a particle. The envelope mass density of a particle of a statistically isotropic shape is defined as the mass of the particle divided by the minimum sphere envelope volume within which it can be enclosed. Features which can contribute to low tap density include irregular surface texture and porous structure.

Tap density can be measured by using instruments known to those skilled in the art such as the Dual Platform Microprocessor Controlled Tap Density Tester (Vankel, N.C.) or a GeoPyc™ instrument (Micrometrics Instrument Corp., Norcross, Ga.). Tap density can be determined using the method of USP Bulk Density and Tapped Density, United States Pharmacopia convention, Rockville, Md., 10$^{th}$ Supplement, 4950-4951, 1999.

Process conditions as well as inhaler efficiency, in particular with respect to dispersibility, can contribute to the size of particles that can be delivered to the pulmonary system. Aerodynamically light particles may be fabricated and then separated, for example, by filtration or centrifugation, to provide a particle sample with a preselected size distribution.

Aerodynamically light particles with a tap density less than about 0.4 g/cm$^3$, median diameters of at least about 5 microns, and an aerodynamic diameter of between about 1 and 5 microns, preferably between about 1 and 3 microns, are more capable of escaping inertial and gravitational deposition in the oropharyngeal region, and are targeted to the airways or the deep lung. The use of larger, more porous particles is advantageous since they are able to aerosolize more efficiently than smaller, denser aerosol particles such as those currently used for inhalation therapies.

In comparison to smaller, relatively dense particles, the larger aerodynamically light particles, preferably having a median diameter of at least about 5 microns, also can potentially more successfully avoid phagocytic engulfinent by alveolar macrophages and clearance from the lungs, due to size exclusion of the particles from the phagocytes' cytosolic space. Phagocytosis of particles by alveolar macrophages diminishes precipitously as particle diameter increases beyond about 3 microns. Kawaguchi, H., et al., *Biomaterials* 7: 61-66 (1986); Krenis, L. J. and Strauss, B., *Proc. Soc. Exp. Med.*, 107: 748-750 (1961); and Rudt, S. and Muller, R. H., *J. Contr Rel.*, 22: 263-272 (1992). For particles of statistically isotropic shape, such as spheres with rough surfaces, the particle envelope volume is approximately equivalent to the volume of cytosolic space required within a macrophage for complete particle phagocytosis.

Aerodynamically light particles thus are capable of a longer term release of an encapsulated agent in the lungs. Following inhalation, aerodynamically light biodegradable particles can deposit in the lungs and subsequently undergo slow degradation and drug release without the majority of the particles being phagocytosed by alveolar macrophages. The drug can be delivered relatively slowly into the alveolar fluid and at a controlled rate into the bloodstream, minimizing possible toxic responses of exposed cells to an excessively high concentration of the drug. The aerodynamically light particles thus are highly suitable for inhalation therapies, particularly in controlled release applications.

The particles may be fabricated with the appropriate material, surface roughness, diameter and tap density for localized delivery to selected regions of the respiratory tract such as the deep lung or upper or central airways. In one embodiment, the particles are amorphous. In another embodiment, the particles are substantially amorphous. In one embodiment the particles are partly to substantially crystalline. In another embodiment, the leucine is crystalline and one or more bioactive ingredients are amorphous. As an example, higher density or larger particles may be used for upper airway delivery, or a mixture of varying sized particles in a sample, provided with the same or different therapeutic agent may be administered to target different regions of the lung in one administration. Particles having an aerodynamic diameter ranging from about 3 to 5 microns are preferred for delivery to the central and upper airways. Particles having an aerodynamic diameter ranging from about 1 to 3 microns are preferred for delivery to the deep lung.

Inertial impaction and gravitational settling of aerosols are predominant deposition mechanisms in the airways and acini of the lungs during normal breathing conditions. (Edwards, D. A., *J. Aerosol Sci.*, 26: 293-317 (1995).) The importance of both deposition mechanisms increases in proportion to the mass of aerosols and not to particle (or envelope) volume. Since the site of aerosol deposition in the lungs is determined by the mass of the aerosol (i.e., at least for particles of mean aerodynamic diameter greater than approximately 1 micron), diminishing the tap density by increasing particle surface irregularities and particle porosity permits the delivery of larger particle envelope volumes into the lungs, all other physical parameters being equal.

The low tap density particles have a small aerodynamic diameter in comparison to the actual envelope sphere diameter. The aerodynamic diameter, $d_{aer}$, is related to the envelope sphere diameter, d (Gonda, I., "Physico-chemical principles in aerosol delivery," in *Topics in Pharmaceutical Sciences* 1991 (eds. D. J. A. Crommelin and K. K. Midha), pp. 95-117, Stuttgart: Medpharm Scientific Publishers, 1992)), by the formula:

$$d_{aer} \propto d\sqrt{r}$$

where the envelope mass density, $\rho$, is in units of g/cm³. Maximal deposition of monodispersed aerosol particles in the alveolar region of the human lung (~60%) occurs for an aerodynamic diameter of approximately $d_{aer}$~3 microns. (Heyder, J., et al., *J. Aerosol Sci.*, 17: 811-825 (1986).) Due to their small envelope mass density, the actual diameter, d, of aerodynamically light particles comprising a monodisperse inhaled powder that will exhibit maximum deep-lung deposition is:

$$d \propto 3/\sqrt{r} \text{(where } \rho < 1 \text{ g/cm}^3\text{)};$$

where d is always greater than about 3 microns. For example, aerodynamically light particles that display an envelope mass density, r=0.1 g/cm³, will exhibit a maximum deposition for particles having envelope diameters as large as 9.5 microns. The increased particle size diminishes interparticle adhesion forces. Visser, J., *Powder Technology*, 58: 1-10. Thus, large particle size increases efficiency of aerosolization to the deep lung for particles of low envelope mass density, in addition to contributing to lower phagocytic losses.

The aerodynamic diameter is calculated to provide for maximum deposition within the lungs, previously achieved by the use of very small particles of less than about 5 microns in diameter, preferably between about 1 and 3 microns, which are then subject to phagocytosis. Selection of particles which have a larger diameter, but which are sufficiently light (hence the characterization "aerodynamically light"), results in an equivalent delivery to the lungs, but the larger size particles are not phagocytosed. Improved delivery can be obtained by using particles with a rough or uneven surface relative to those with a smooth surface.

Mass density and the relationship between mass density, mean diameter and aerodynamic diameter are discussed in U.S. application Ser. No. 08/655,570, filed on May 24, 1996, which is incorporated herein by reference in its entirety.

In a preferred embodiment, the particles of the invention can be characterized by their solid state stability. The solid state stability of the particles can be an indicator of overall physical stability. Physical stability can effect important characteristics of a pharmaceutical composition including shelf-life, proper storage conditions, acceptable environments for administration, and efficiency of administration. Solid state stability can be assessed using techniques well known in the art. Particularly helpful techniques are differential scanning calorimetry (DSC), dynamic vapor sorption (DVS), x-ray diffraction (XRD), and thermal stress testing.

In a preferred embodiment, particles of the invention demonstrate physical stability when exposed to humidity. Physical stability upon exposure to humidity can be assessed using dynamic vapor sorption (DVS). Using DVS, moisture sorption isotherms are generated by exposing a material to a flow of humidified gas. Water uptake by the material is measured gravimetrically. The DVS-1000 from Surface Measurement Systems (London, United Kingdom) is one example of a commercial DVS system.

In one embodiment, the particles exhibit relatively low powder hygroscopicity. Powder hygroscopicity can be examined by using DVS. For example, powder can be exposed to a stream of humid air that gradually ramps from 20% to 90% relative humidity (RH) over 1.5 hours. The maximum weight gain of the powder during such a ramp can be indicative of powder hygroscopicity. In one embodiment, the powders of the invention exhibit less than about 8% water uptake while exposed to humid air during a gradual ramp up to about 90% RH. In a preferred embodiment, the powders of the invention exhibit less than about 6% water uptake while exposed to humid air during a gradual ramp up to about 90% RH. Even more preferred, the powders of the invention exhibit less than about 4% water uptake while exposed to humid air during a ramp up to about 90% RH.

In another embodiment, the particles resist irreversible physical changes occurring in the powder as a result of exposure to humidity. DVS can be used to evaluate irreversible physical changes caused by humidity. For example, powder can be exposed to a stream of humid air that gradually ramps from 20% to 90% RH, ramps from 90% to 20% RH; holds at 20% RH, ramps from 20% to 90% RH and then again ramps from 90% to 20% RH. Differences between the maximum weight gain during the first ramp up to 90% RH and the maximum weight gain during the second ramp up to 90% RH can indicate irreversible physical changes in the powder.

The most common changes that occur in powders due to water sorption are amorphous-crystalline conversions. Without being held to a particular theory, it is believed that since amorphous phase regions tend to absorb more water than crystalline phase regions, a decreased maximum percent weight gain during the second ramp thus indicates a decreased amount of amorphous phase present in the powder.

In a preferred embodiment, the particles of the present invention exhibit small or no differences in maximum water uptake upon humidity cycling. Thus, in a preferred embodiment, the particles of the instant invention possess an amorphous phase that is stable upon exposure to humidity, a crystalline phase, a semi-crystalline phase, or a combination thereof. Preferably, particles of the present invention exhibit differences in maximum weight gain of less than about 1% when subjected to repeated cycling of humidity up to about 90% RH. Even more preferably, particles of the present invention exhibit differences in maximum weight gain of less than about 0.5% when subjected to repeated cycling of humidity up to about 90% RH.

In a preferred embodiment, particles of the invention exhibit few or no changes in crystallinity when exposed to air of 75% relative humidity. As is well known in the art, crystallinity changes in powders can be evaluated using a technique such as x-ray diffraction (XRD).

Powder solid state stability can also be evaluated by analyzing thermal transitions. Thermal transitions can be measured using differential scanning calorimetry (DSC). In a preferred embodiment, the particles of the invention have phase transition temperatures, e.g., melting temperature ($T_m$), crystallization temperature ($T_c$), or glass transition temperature ($T_g$), that are at least about 40° C., greater than about 60° C., or most preferably greater than about 100° C. Particles having phase transition temperatures of at least about 50° C. are preferred to ensure powder stability upon powder receptacle filling and sealing, to ensure powder stability upon powder exposure to stressed environmental conditions (e.g., exposure to high storage or shipping temperatures), and to reduce the potential for chemical instability.

In one embodiment, the particles of the invention are able to withstand thermal stresses up to about 55° C. for up to about six hours. The ability of a powder to withstand thermal stress can be measured, for example, by subjecting a powder to elevated temperatures and subsequently measuring fine particle fraction of the powder. An instrument such as an Andersen Cascade Impactor can be used to measure fine particle fraction.

In one embodiment, a mass of particles subjected to temperatures up to about 45° C. for up to about six hours exhibit FPF(<5.6) that vary from FPF(<5.6) of a mass of similar particles held at room temperature by less than about 25%. In a preferred embodiment, a mass of particles, held at a temperature of at least about 45° C. for six hours, has a FPF(<5.6) that varies from the FPF(<5.6) of a mass of similar particles held at room temperature by less than about 15%.

In another embodiment, a mass of particles subjected to temperatures up to about 55° C. for up to about six hours exhibit FPF(<5.6) that vary from FPF(<5.6) of a mass of similar particles held at room temperature by less than about 25%. In a preferred embodiment, a mass of particles, held at a temperature of at least about 55° C. for six hours, has a FPF(<5.6) that varies from the FPF(<5.6) of a mass of similar particles held at room temperature by less than about 20%.

In one embodiment, the particles of the invention can be characterized by the chemical stability of the therapeutic, prophylactic or diagnostic agents that comprise the particles. Without being held to any particular theory, it is believed that several factors can influence the chemical stability of a constituent agent. These factors can include the materials comprising the particles, the stability of the agent itself, interactions between the agent and excipients, and interactions between agents. The chemical stability of a constituent therapeutic, prophylactic or diagnostic agent can effect important characteristics of a pharmaceutical composition including shelf-life, proper storage conditions, acceptable environments for administration, biological compatibility, and effectiveness of the agent. Chemical stability can be assessed using techniques well known in the art. One example of a technique that can be used to assess chemical stability is reverse phase high performance liquid chromatography (HPLC).

In a preferred embodiment, the particles of the invention do not exhibit substantial degradation of ipratropium or salmeterol (i.e., impurity concentration is less than about 5% total impurities by weight) after being stored, either at about 15% RH or sealed in packaging at about 75% RH, at temperatures up to about 40° C. for up to about three months.

In one embodiment, the particles of the present invention comprise one or more therapeutic, prophylactic or diagnostic agents. Therapeutic, prophylactic or diagnostic agents are also referred to herein as "bioactive agents," "medicaments" or "drugs." The agent or combination of agents can be capable of possessing an overall net charge. In a preferred embodiment, the therapeutic, prophylactic or diagnostic agents are ipratropium bromide and salmeterol xinafoate.

In one aspect, the present invention relates to particles for drug delivery via the pulmonary system and a method of therapy comprising administering to the respiratory tract of a patient in need of treatment, prophylaxis or diagnosis an effective amount of particles wherein the particles comprise about 5 to 10 weight percent of salmeterol xinafoate; about 4 to 15 weight percent of ipratropium bromide; about 2 to 8 weight percent of 1,2-Dipalmitoyl-sn-glycero-3-phosphocholine (DPPC); about 1 to 8 weight percent of 1,2-Distearoyl-sn-glycero-3-phosphocholine (DSPC); and about 60 to 80 weight percent of leucine.

In one embodiment, salmeterol xinafoate is present in a concentration of about 5 to 8 weight percent. Preferably, salmeterol xinafoate is present in a concentration of about 6 weight percent. In another embodiment, ipratropium bromide is present in a concentration of about 10 to 15 weight percent. In another, ipratropium bromide is present in a concentration of about 12 to 14 weight percent. Preferably, ipratropium bromide is present in a concentration of about 13 weight percent.

In another embodiment, 1,2-Dipalmitoyl-sn-glycero-3-phosphocholine (DPPC) is present in a concentration of about 5 to 8 weight percent. Preferably, DPPC is present in a concentration of about 5 weight percent. In another embodiment, 1,2-Distearoyl-sn-glycero-3-phosphocholine (DSPC) is present in a concentration of about 5 to 8 weight percent. Preferably, DSPC is present in a concentration of about 5 weight percent. In another embodiment, leucine is present in a concentration of about 70 to 80 weight percent. Preferably, leucine is present in a concentration of about 71 weight percent.

In a preferred embodiment, the weight ratio of leucine to 1,2-Dipalmitoyl-sn-glycero-3-phosphocholine (DPPC) to 1,2-Distearoyl-sn-glycero-3-phosphocholine (DSPC) is about 72 to 5 to 5. In some embodiments, the weight ratio of salmeterol xinafoate to ipratropium bromide can be about 2:1 to 1:5, such as, for example, 3:2, 1:1, 1:2; 1:3, or 1:5. Preferably, the weight ratio of salmeterol xinafoate to ipratropium bromide is about 3:2 to 1:2, or about 1.5 to 0.5.

In another aspect, the present invention relates to particles for drug delivery via the pulmonary system and a method of therapy comprising administering to the respiratory tract of a patient in need of treatment, prophylaxis or diagnosis an effective amount of particles wherein the particles comprise about 5 to 10 weight percent of salmeterol xinafoate; about 4 to 15 weight percent of ipratropium bromide; about 2 to 8 weight percent of 1,2-Dipalmitoyl-sn-glycero-3-phosphocholine (DPPC); and about 68 to 88 weight percent of leucine.

In a preferred embodiment, the weight ratio of 1,2-Dipalmitoyl-sn-glycero-3-phosphocholine (DPPC) to leucine is about 5 to 76. In some embodiments, the weight ratio of salmeterol xinafoate to ipratropium bromide can be about 2:1 to 1:5, such as, for example, 3:2, 1:1, 1:2; 1:3, or 1:5. Preferably, the weight ratio of salmeterol xinafoate to ipratropium bromide is about 3:2 to 1:2, or about 1.5 to 0.5.

In one preferred embodiment, the particles comprise about 6 weight percent of salmeterol xinafoate; about 13 weight percent of ipratropium bromide; about 5 weight percent of 1,2-Dipalmitoyl-sn-glycero-3-phosphocholine (DPPC); and about 76 weight percent of leucine.

In one aspect, the present invention relates to particles for drug delivery via the pulmonary system and a method of therapy comprising administering to the respiratory tract of a patient in need of treatment, prophylaxis or diagnosis an effective amount of particles wherein the particles comprise about 5 to 10 weight percent of salmeterol xinafoate; about 4 to 15 weight percent of ipratropium bromide; about 5 to 15 weight percent of 1,2-Dipalmitoyl-sn-glycero-3-phosphocholine (DPPC); about 20 to 40 weight percent of 1,2-Distearoyl-sn-glycero-3-[phospho-rac-(1-glycerol)] (DSPG); and about 30 to 60 weight percent of leucine.

In one embodiment, salmeterol xinafoate is present in a concentration of about 5 to 8 weight percent. Preferably, salmeterol xinafoate is present in a concentration of about 6 weight percent. In another embodiment, ipratropium bromide is present in a concentration of about 10 to 15 weight percent. In another, ipratropium bromide is present in a concentration of about 12 to 14 weight percent. Preferably, ipratropium bromide is present in a concentration of about 13 weight percent.

In another embodiment, 1,2-Dipalmitoyl-sn-glycero-3-phosphocholine (DPPC) is present in a concentration of about 9 to 14 weight percent or about 10 to 13 weight percent. Preferably, DPPC is present in a concentration of about 11 weight percent. In another embodiment, 1,2-Distearoyl-sn-glycero-3-[phospho-rac-(1-glycerol)] (DSPG) is present in a concentration of about 27 to 37 weight percent or about 29 to 37 weight percent. Preferably, DSPG is present in a concentration of about 32 weight percent. In another embodiment, leucine is present in a concentration of about 35 to 45 weight percent or about 35 to 43 weight percent. Preferably, leucine is present in a concentration of about 38 weight percent.

In a preferred embodiment, the weight ratio of leucine to 1,2-Dipalmitoyl-sn-glycero-3-phosphocholine (DPPC) to 1,2-Distearoyl-sn-glycero-3-[phospho-rac-(1-glycerol)] (DSPG) is about 42 to 12 to 35. In some embodiments, the weight ratio of saimeterol xinafoate to ipratropium bromide can be about 2:1 to 1:5, such as, for example, 3:2, 1:1, 1:2; 1:3, or 1:5. Preferably, the weight ratio of salmeterol xinafoate to ipratropium bromide is about 3:2 to 1:2, or about 1.5 to 0.5.

In one aspect, the present invention relates to particles for drug delivery via the pulmonary system and a method of therapy comprising administering to the respiratory tract of a patient in need of treatment, prophylaxis or diagnosis an effective amount of particles wherein the particles comprise about 5 to 10 weight percent of salmeterol xinafoate; about 4 to 15 weight percent of ipratropium bromide; about 10 to 20 weight percent of 1-Myristoyl-2-stearoyl-sn-glycero-3-phosphocholine (MSPC); about 20 to 40 weight percent of 1,2-Dimyristoyl-sn-glycero-3-phosphoethanolamine (DMPE); and about 35 to 60 weight percent of leucine.

In one embodiment, salmeterol xinafoate is present in a concentration of about 5 to 8 weight percent. Preferably, salmeterol xinafoate is present in a concentration of about 6 weight percent. In another embodiment, ipratropium bromide is present in a concentration of about 10 to 15 weight percent. In another, ipratropium bromide is present in a concentration of about 12 to 14 weight percent. Preferably, ipratropium bromide is present in a concentration of about 13 weight percent.

In another embodiment, 1-Myristoyl-2-stearoyl-sn-glycero-3-phosphocholine (MSPC) is present in a concentration of about 10 to 15 weight percent or about 10 to 13 weight percent. Preferably, MSPC is present in a concentration of about 11 weight percent. In another embodiment, 1,2-Dimyristoyl-sn-glycero-3-phosphoethanolamine (DMPE) is present in a concentration of about 30 to 40 weight percent or about 31 to 39 weight percent. Preferably, DMPE is present in a concentration of about 34 weight percent. In another embodiment, leucine is present in a concentration of about 30 to 40 weight percent or about 33 to 40 weight percent. Preferably, leucine is present in a concentration of about 36 weight percent.

In a preferred embodiment, the weight ratio of leucine to 1-Myristoyl-2-stearoyl-sn-glycero-3-phosphocholine (MSPC) to 1,2-Dimyristoyl-sn-glycero-3-phosphoethanolamine (DMPE) is about 39 to 12 to 37. In some embodiments, the weight ratio of salmeterol xinafoate to ipratropium bromide can be about 2:1 to 1:5, such as, for example, 3:2, 1:1, 1:2; 1:3, or 1:5. Preferably, the weight ratio of salmeterol xinafoate to ipratropium bromide is about 3:2 to 1:2, or about 1.5 to 0.5.

In one aspect, the present invention relates to particles for drug delivery via the pulmonary system and a method of therapy comprising administering to the respiratory tract of a patient in need of treatment, prophylaxis or diagnosis an effective amount of particles wherein the particles comprise about 5 to 10 weight percent of salmeterol xinafoate; about 4 to 15 weight percent of ipratropium bromide; and about 75 to 91 weight percent of leucine.

In one embodiment, salmeterol xinafoate is present in a concentration of about 5 to 8 weight percent. Preferably, salmeterol xinafoate is present in a concentration of about 6 weight percent. In another embodiment, ipratropium bromide is present in a concentration of about 10 to 15 weight percent. In another, ipratropium bromide is present in a concentration of about 12 to 14 weight percent. Preferably, ipratropium bromide is present in a concentration of about 13 weight percent.

In another embodiment, leucine is present in a concentration of about 75 to 85 weight percent. In another embodiment, leucine is present in a concentration of about 79 to 83 weight percent. Preferably, leucine is present in a concentration of about 81 weight percent.

In some embodiments, the weight ratio of salmeterol xinafoate to ipratropium bromide can be about 2:1 to 1:5, such as, for example, 3:2, 1:1, 1:2; 1:3, or 1:5. Preferably, the weight ratio of salmeterol xinafoate to ipratropium bromide is about 3:2 to 1:2, or about 1.5 to 0.5.

In one aspect, the present invention relates to particles for drug delivery via the pulmonary system and a method of therapy comprising administering to the respiratory tract of a patient in need of treatment, prophylaxis or diagnosis an effective amount of particles wherein the particles comprise about 5 to 10 weight percent of saimeterol xinafoate; about 4 to 15 weight percent of ipratropium bromide; about 2 to 10 weight percent of mannitol; and about 65 to 85 weight percent of leucine.

In one embodiment, salmeterol xinafoate is present in a concentration of about 5 to 8 weight percent. Preferably, salmeterol xinafoate is present in a concentration of about 6 weight percent. In another embodiment, ipratropium bromide is present in a concentration of about 10 to 15 weight percent. In another, ipratropium bromide is present in a concentration of about 12 to 14 weight percent. Preferably, ipratropium bromide is present in a concentration of about 13 weight percent.

In another embodiment, mannitol is present in a concentration of about 5 to 9 weight percent, or about 6 to 9 weight percent. Preferably, mannitol is present in a concentration of about 7 weight percent. In another embodiment, leucine is present in a concentration of about 70 to 80 weight percent. Preferably, leucine is present in a concentration of about 74 weight percent.

In a preferred embodiment, the weight ratio of leucine to mannitol is about 10 to 1. In some embodiments, the weight ratio of salmeterol xinafoate to ipratropium bromide can be about 2:1 to 1:5, such as, for example, 3:2, 1:1, 1:2; 1:3, or 1:5. Preferably, the weight ratio of salmeterol xinafoate to ipratropium bromide is about 3:2 to 1:2, or about 1.5 to 0.5.

In one embodiment of the invention, particles comprise one or more amino acids. Hydrophobic amino acids are preferred. In one embodiment, the particles comprise the amino acid leucine or an analog thereof. Other suitable amino acids include naturally occurring and non-naturally occurring hydrophobic amino acids. Non-naturally occurring amino acids include, for example, beta-amino acids. Both D, L and racemic configurations of hydrophobic amino acids can be employed. Suitable hydrophobic amino acids can also include amino acid analogs. As used herein, an amino acid analog includes the D or L configuration of an amino acid having the following formula: —NH—CHR—CO—, wherein R is an aliphatic group, a substituted aliphatic group, a benzyl group, a substituted benzyl group, an aromatic group or a substituted aromatic group and wherein R does not correspond to the side chain of a naturally-occurring amino acid. As used herein, aliphatic groups include straight chained, branched or cyclic C1-C8 hydrocarbons which are completely saturated, which contain one or two heteroatoms such as nitrogen, oxygen or sulfur and/or which contain one or more units of desaturation. Aromatic groups include carbocyclic aromatic groups such as phenyl and naphthyl and heterocyclic aromatic groups such as imidazolyl, indolyl, thienyl, furanyl, pyridyl, pyranyl, oxazolyl, benzothienyl, benzofuranyl, quinolinyl, isoquinolinyl and acridintyl.

Suitable substituents on an aliphatic, aromatic or benzyl group include —OH, halogen (e.g., —Br, —Cl, —I and —F), —O(aliphatic, substituted aliphatic, benzyl, substituted benzyl, aryl or substituted aryl group), —CN, —NO$_2$, —COOH, —NH$_2$, —NH(aliphatic group, substituted aliphatic, benzyl, substituted benzyl, aryl or substituted aryl group), —N(aliphatic group, substituted aliphatic, benzyl, substituted benzyl, aryl or substituted aryl group)$_2$, —COO(aliphatic group, substituted aliphatic, benzyl, substituted benzyl, aryl or substituted aryl group), —CONH$_2$, —CONH(aliphatic, substituted aliphatic group, benzyl, substituted benzyl, aryl or substituted aryl group), —SH, —S(aliphatic, substituted aliphatic, benzyl, substituted benzyl, aromatic or substituted aromatic group) and —NH—C(=NH)—NH$_2$. A substituted benzylic or aromatic group can also have an aliphatic or substituted aliphatic group as a substituent. A substituted aliphatic group can also have a benzyl, substituted benzyl, aryl or substituted aryl group as a substituent. A substituted aliphatic, substituted aromatic or substituted benzyl group can have one or more substituents. Modifying an amino acid substituent can increase, for example, the lypophilicity or hydrophobicity of natural amino acids which are hydrophilic.

A number of the suitable amino acids, amino acids analogs and salts thereof can be obtained commercially. Others can be synthesized by methods known in the art. Synthetic techniques are described, for example, in Greene and Wuts, "*Protecting Groups in Organic Synthesis,*" John Wiley and Sons, Chapters 5 and 7 (1991).

Hydrophobicity is generally defined with respect to the partition of an amino acid between a nonpolar solvent and water. Hydrophobic amino acids are those acids which show a preference for the nonpolar solvent. Relative hydrophobicity of amino acids can be expressed on a hydrophobicity scale on which glycine has the value 0.5. On such a scale, amino acids which have a preference for water have values below 0.5 and those that have a preference for nonpolar solvents have a value above 0.5. As used herein, the term "hydrophobic amino acid" refers to an amino acid that, on the hydrophobicity scale, has a value greater or equal to 0.5, in other words, has a tendency to partition in the nonpolar acid which is at least equal to that of glycine.

Examples of amino acids which can be employed include, but are not limited to: glycine, proline, alanine, cysteine, methionine, valine, leucine, tyrosine, isoleucine, phenylalanine, and tryptophan. Preferred hydrophobic amino acids include leucine, isoleucine, alanine, valine, phenylalanine and glycine. Combinations of hydrophobic amino acids can also be employed. Furthermore, combinations of hydrophobic and hydrophilic (preferentially partitioning in water) amino acids, where the overall combination is hydrophobic, can also be employed.

The amino acid can be present in the particles of the invention in an amount of at least 10 weight percent. Preferably, the amino acid is leucine and is present in the particles in an amount ranging from about 30 to 91 weight percent. The salt of a hydrophobic amino acid can be present in the particles of the invention in an amount of at least 10 weight percent. Preferably, a leucine salt is present in the particles in an amount ranging from about 30 to 91 weight percent. In preferred embodiments the particles have a tap density of less than about 0.4 g/cm$^3$.

In another embodiment, the particles comprise at least about 46 weight percent leucine. In some embodiments, the particles comprise about 80 to 95 weight percent leucine, about 65 to 80 weight percent leucine, or about 50 to 65 weight percent leucine. In one embodiment, the particles comprise about 46 to 50 weight percent leucine. In yet another embodiment, the particles comprise about 46 weight percent leucine.

In one preferred embodiment, the particles are spray dried and comprise the hydrophobic amino acid leucine. Without being held to any particular theory, it is believed that due to their hydrophobicity and low water solubility, hydrophobic amino acids, such as leucine, facilitate the formation of a shell during the drying process when an ethanol:water co-solvent is employed. It is also believed that the amino acids may alter the phase behavior of any phospholipids present in such a way as to facilitate the formation of a shell during the drying process.

Methods of forming and delivering particles which include an amino acid are described in U.S. patent application Ser. No. 09/382,959, filed on Aug. 25, 1999, entitled "Use of Simple Amino Acids to Form Porous Particles During Spray Drying," the teachings of which are incorporated herein by reference in their entirety.

The phospholipid, can be present in the particles in an amount ranging from about 0 to 90 weight percent. More commonly it can be present in the particles in an amount ranging from about 10 to 60 weight percent.

The particles of the present invention can comprise a charged phospholipid. The term "charged phospholipid," as used herein, refers to phospholipids which are capable of possessing an overall net charge. The charge on the phospholipid can be negative or positive. The phospholipid can be chosen to have a charge opposite to that of a therapeutic, diagnostic or prophylactic agent when the phospholipid and agent are associated. Preferably, the phospholipid is endogenous to the lung or can be metabolized upon administration to a lung endogenous phospholipid. Combinations of charged phospholipids can be used. The combination of charged phospholipids can also have an overall net charge opposite to that of the therapeutic, diagnostic or prophylactic agent upon association. Not being held to any particular theory, Applicants believe, for example, that ipratropium, having a positive charge, associates with the combination of DSPG and DPPC, having a net negative charge.

In one embodiment, the association of a therapeutic, prophylactic or diagnostic agent and an oppositely charged lipid can result from ionic complexation. In another embodiment, association of a therapeutic, prophylactic or diagnostic agent and an oppositely charged lipid can result from hydrogen bonding. In yet a further embodiment, the association of a therapeutic, prophylactic or diagnostic agent and an oppositely charged lipid can result from a combination of ionic complexation and hydrogen bonding.

The charged phospholipid can be a negatively charged lipid such as, a 1,2-diacyl-sn-glycero-3-[phospho-rac-(1-glycerol)].

The 1,2-diacyl-sn-glycero-3-[phospho-rac-(1-glycerol)] phospholipids can be represented by Formula I:

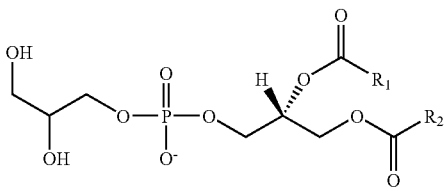

wherein $R_1$ and $R_2$ are each independently an aliphatic group having from about 3 to 24 carbon atoms, preferably from about 10 to 20 carbon atoms.

"Aliphatic group" as that term is used herein in reference to Formulas I-IV refers to substituted or unsubstituted straight chained, branched or cyclic $C_1$-$C_{24}$ hydrocarbons which can be completely saturated, which can contain one or more heteroatoms such as nitrogen, oxygen or sulfur and/or which can contain one or more units of unsaturation.

Suitable substituents on an aliphatic group include —OH, halogen (e.g., —Br, —Cl, —I and —F) —O(aliphatic, substituted), —CN, —NO$_2$, —COOH, —NH$_2$, —NH(aliphatic group, substituted aliphatic), —N(aliphatic group, substituted aliphatic group)$_2$, —COO(aliphatic group, substituted aliphatic group), —CONH$_2$, —CONH(aliphatic, substituted aliphatic group), —SH, —S(aliphatic, substituted aliphatic group) and —NH—C(=N)—NH$_2$. A substituted aliphatic group can also have a benzyl, substituted benzyl, aryl (e.g., phenyl, naphthyl or pyridyl) or substituted aryl group as a substituent. A substituted aliphatic can have one or more substituents.

Specific examples of this type of negatively charged phospholipid include, but are not limited to, 1,2-distearoyl-sn-glycero-3-[phospho-rac-(1-glycerol)] (DSPG); 1,2-dimyristoyl-sn-glycero-3-[phospho-rac-(1-glycerol)] (DMPG); 1,2-dipalmitoyl-sn-glycero-3-phospho-rac-(1-glycerol)] (DPPG); 1,2-dilauroyl-sn-glycero-3-[phospho-rac-(1-glycerol)] (DLPG); and 1,2-dioleoyl-sn-glycero-3-[phospho-rac-(1-glycerol)] (DOPG).

The particles of the invention can also comprise phospholipids which are zwitterionic and therefore do not possess an overall net charge. Such lipids can assist in providing particles with the proper characteristics for inhalation. Such phospholipids suitable for use in the invention include, but are not limited to, 1,2-diacyl-sn-glycero-3-phosphocholine and 1,2-diacyl-sn-glycero-3-phosphoethanolamine.

The 1,2-diacyl-sn-glycero-3-phosphocholine phospholipids can be represented by

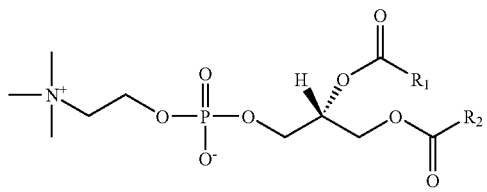

$R_1$ and $R_2$ are each independently an aliphatic group having from about 3 to 24 carbon atoms, preferably from about 10 to 20 carbon atoms.

Specific examples of 1,2-diacyl-sn-glycero-3-phosphocholine phospholipids include, but are not limited to, 1,2-dipalmitoyl-sn-glycero-3-phosphocholine (DPPC); 1,2-distearoyl-sn-glycero-3-phosphocholine (DSPC); 1,2-dilaureoyl-sn-3-glycero-phosphocholine (DLPC); 1,2-dimyristoyl-sn-glycero-3-phosphocholine (DMPC); and 1,2-dioleoyl-sn-glycero-3-phosphocholine (DOPC).

The 1,2-diacyl-sn-glycero-3-phosphoalkanolamine phospholipids can be represented by Formula III:

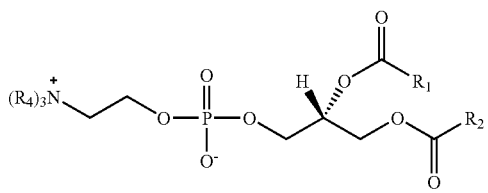

wherein $R_1$ and $R_2$ are each independently an aliphatic group having from about 3 to 24 carbon atoms, preferably, from about 10 to 20 carbon atoms and $R_4$ is independently hydrogen or an aliphatic group having from about 1 to 6 carbon atoms.

Specific examples of this type of phospholipid include, but are not limited to, 1,2-dipalmitoyl-sn-glycero-3-ethanolamine(DPPE); 1,2-dimyristoyl-sn-glycero-3-phosphoethanolamine(DMPE); 1,2-distearoyl-sn-glycero-3-phosphoethanolamine(DSPE); 1,2-dilauroyl-sn-glycero-3-phosphoethanolamine (DLPE); and 1,2-dioleoyl-sn-glycero-3-phosphoethanolamine (DOPE).

The particles of the present invention can comprise an asymmetric phospholipid, such as a 1-acyl, 2-acyl-sn-glycero-3-phosphocholine.

The 1-acyl,2-acyl-sn-glycero-3-phosphocholine phospholipids can be represented by Formula IV:

$$\underset{\text{structure}}{}$$

wherein $R_1$ and $R_2$ are each independently an aliphatic group having from about 3 to 24 carbon atoms and wherein the aliphatic groups represented by $R_1$ and $R_2$ have differing carbon chain lengths. Preferably, $R_1$ and $R_2$ have from about 10 to 20 carbon atoms.

Specific examples of this type of phospholipid include, but are not limited to, 1-palmitoyl-2-stearoyl-sn-glycero-3-phosphocholine (PSPC); 1-stearoyl-2-palmitoyl-sn-glycero-3-phosphocholine (SPPC); 1-stearoyl-2-myristoyl-sn-glycero-3-phosphocholine (SMPC); 1-myristoyl-2-stearoyl-sn-glycero-3-phosphocholine (MSPC); 1-myristoyl-2-palmitoyl-sn-glycero-3-phosphocholine (MPPC); and 1-palmitoyl-2-myristoyl-sn-glycero-3-phosphocholine (PMPC).

"Asymmetric phospholipids" are also known to those experienced in the art as "mixed-chain" or "non-identical chain" phospholipids.

Particles of the present invention may comprise combinations of asymmetric phospholipids, combinations of symmetric phospholipids, or combinations of asymmetric and symmetric phospholipids. In one preferred embodiment, the particles comprise one asymmetric phospholipid and one symmetric phospholipid.

In a preferred embodiment of the present invention, particles comprise asymmetric phospholipids having individual acyl chains that are naturally present in the lung. Particles comprising disaturated phospholipids are preferred over particles comprising mono- or di-unsaturated phospholipids.

Without being held to any particular theory, Applicants believe that particles containing asymmetric phospholipids may possess unique packing and/or partition of constituent therapeutic, prophylactic or diagnostic agent or agents and result in entrapment or encapsulation of the drug. It is thought that drug release and subsequent uptake of the drug payload from the aerosol formulation will be slower if the drug is entrapped or encapsulated rather than simply surface-associated. Applicants believe that for entrapped or encapsulated drug molecules, the availability of the agent in the dissolution media or physiological lining fluids is not only determined by drug solubility but also by particle dissolution and/or diffusion of drug molecules from the particle matrix. In contrast, it is believed that in particles in which drug molecules are primarily surface associated, the availability of drug molecules is primarily drug solubility limited. Consequently, entrapment or encapsulation of the drug in the particle matrix may slow release and subsequent uptake of the drug.

Particles comprising asymmetric phospholipids are described in U.S. Patent Application No. 60/359,466, entitled "Sustained Release Formulations Utilizing Asymmetric Phospholipids," filed on Feb. 22, 2002, the contents of which are incorporated herein in their entirety.

In one embodiment, the particles can also include other materials such as, for example, buffer salts, cholesterol, dextran, polysaccharides, lactose, trehalose, sucrose, mannitol, maltodextrin, cyclodextrins, proteins, peptides, polypeptides, fatty acids, fatty acid esters, inorganic compounds, phosphates, lipids, polyethylene glycol, precirol, and polymers.

The particles and respirable compositions comprising the particles of the invention may optionally include a surfactant, such as a surfactant which is endogenous to the lung. As used herein, the term "surfactant" refers to any agent which preferentially absorbs to an interface between two immiscible phases, such as the interface between water and an organic polymer solution, a water/air interface or organic solvent/air interface. Surfactants generally possess a hydrophilic moiety and a lipophilic moiety, such that, upon absorbing to microparticles, they tend to present moieties to the external environment that do not attract similarly-coated particles, thus reducing particle agglomeration. Both naturally-occurring and synthetic lung surfactants are encompassed in the scope of the invention.

In addition to lung surfactants, such as, for example, phospholipids discussed above, suitable surfactants include but are not limited to hexadecanol; fatty alcohols such as polyethylene glycol (PEG); polyoxyethylene-9-lauryl ether; a surface active fatty acid, such as palmitic acid or oleic acid; glycocholate; surfactin; a poloxomer; a sorbitan fatty acid ester such as sorbitan trioleate (Span 85); and tyloxapol.

A surfactant can be present in the particles in an amount ranging from about 1 to about 46 weight percent. In an alternative embodiment a surfactant may be present in an amount of from 2 to 90 weight percent. In one embodiment, about 10 to 40 weight percent. In another embodiment, a surfactant is present in the particles in an amount of about 20 to 46 weight percent.

Methods of preparing and administering particles which are aerodynamically light and include surfactants, and, in particular phospholipids, are disclosed in U.S. Pat. No. 5,855,913, issued on Jan. 5, 1999 to Hanes, et al, and in U.S. Pat. No. 5,985,309, issued on Nov. 16, 1999 to Edwards, et al. The contents of both issued patents are incorporated herein in their entirety, by reference.

Highly dispersible particles suitable for use in the methods of the invention may be prepared using single and double emulsion solvent evaporation, spray drying, solvent extraction, solvent evaporation, phase separation, simple and complex coacervation, interfacial polymerization, supercritical carbon dioxide ($CO_2$) and other methods well known to those of ordinary skill in the art. Particles may be made using methods for making microspheres or microcapsules known in the art, provided that the conditions are optimized for forming particles with the desired aerodynamic properties (e.g., a particular aerodynamic diameter) or additional steps are performed to select particles with the density and diameter sufficient to provide the particles with an aerodynamic diameter between about 1 and 5 microns, preferably between about 1 and 3 microns.

If the particles prepared by any of the above methods have a size range outside of the desired range, particles can be sized, for example, using a sieve, and further separated according to density using techniques known to those of skill in the art.

The particles are preferably spray dried. Suitable spray-drying techniques are described, for example, by K. Masters in "Spray Drying Handbook", John Wiley & Sons, New York (1984). Generally, during spray-drying, heat from a hot gas such as heated air or nitrogen is used to evaporate a solvent from droplets formed by atomizing a continuous liquid feed.

An organic solvent or an aqueous-organic solvent can be employed to form a feed for spray drying the particles of the present invention.

Suitable organic solvents that can be employed include but are not limited to alcohols such as, for example, ethanol, methanol, propanol, isopropanol, butanolsh, and others. Other organic solvents include but are not limited to perfluorocarbons, dichloromethane, chloroform, ether, ethyl acetate, methyl tert-butyl ether and others.

Co-solvents that can be employed include an aqueous solvent and an organic solvent, such as, but not limited to, the organic solvents as described above. Aqueous solvents include water and buffered solutions. In one embodiment, an ethanol/water solvent is preferred with the ethanol solution to water solution ratio ranging from about 70:30 to about 30:70 by volume.

The mixture can have a neutral, acidic or alkaline pH. Optionally, a pH buffer can be added to the solvent or co-solvent or to the formed mixture. Preferably, the pH can range from about 5 to 8.

In one embodiment, organic soluble particle components are dissolved in an organic phase and water soluble particle components are dissolved in an aqueous phase. The solutions are heated as necessary to assure solubility. In a preferred embodiment, ethanol soluble particle components are dissolved in an ethanol phase and water soluble particle components are dissolved in an aqueous phase.

In one embodiment, solutions containing particle components are combined or mixed prior to spray drying. For example, in one aspect of the present invention the solutions are bulk mixed prior to being fed to the spray dryer. In one embodiment, the solutions are combined or mixed such that the resulting solution has a total dissolved solids concentration of about 1 g per L of resulting solution. Preferably, the dissolved solids concentration is greater than about 1 g per L of resulting solution, for example, about 5, 10, or 15 g per L of solution. In another embodiment, solutions containing particle components are combined or mixed using a static mixing device prior to spray drying.

In one aspect of the present invention, a hydrophillic component and a hydrophobic component are prepared. The hydrophobic and hydrophilic components are then combined in a static mixer to form a combination. The combination is atomized to produce droplets, which are dried to form dry particles. In a preferred aspect of this method, the atomizing step is performed immediately after the components are combined in the static mixer. In another preferred aspect of this method, the hydrophilic component comprises an active agent, including, but not limited to suitable agents referred to above.

In a further aspect of the present invention, a method for preparing a dry powder composition is provided. In such a method, first and second components are prepared, one or both of which comprise an active agent. The first and second components are combined in a static mixer to form a combination. In one embodiment, the first and second components are physically and/or chemically incompatible with each other. In one aspect, the first and second components are such that combining them causes degradation in one of the components. In another aspect, a material present in the first component is incompatible with a material present in the second component. The combination is atomized to produce droplets that are dried to form dry particles. In a preferred aspect of such a method, the first component comprises an active agent and one or more excipients dissolved in an aqueous solvent, and the second component comprises an active agent and one or more excipients dissolved in an organic solvent.

In yet a further aspect of the present invention, a method for preparing a dry powder composition is provided. In such a method, a first phase is prepared that comprises water, ipratropium bromide, leucine, and, optionally, mannitol. A second phase is prepared that comprises salmeterol xinafoate, one or more phospholipids and ethanol. One or both solutions may be separately heated as needed to assure solubility of their components. Both solutions are heated to assure solubility of their components. The first and second phases are combined in a static mixer to form a combination. The combination is atomized to produce droplets that are dried to form dry particles.

Alternatively, in such a method, a first phase is prepared that comprises water, albuterol sulfate, leucine, and, optionally sucrose. A second phase is prepared that comprises one or more phospholipids and ethanol.

In a preferred embodiment, the apparatus used for practice of the present invention includes a static mixer (e.g., a static mixer as more fully described in U.S. Pat. No. 4,511,258, the contents of which are incorporated in their entirety herein by reference, or other suitable static mixers such as, but not limited to, Model 1/4-21, made by Koflo Corporation.) having an inlet end and an outlet end. The static mixer is operative to combine an aqueous component with an organic component to form a combination. Means are provided for transporting the aqueous component and the organic component to the inlet end of the static mixer. In a preferred aspect, the aqueous and organic components are transported to the static mixer at substantially the same rate. An atomizer is in fluid communication with the outlet end of the static mixer to atomize the combination into droplets. The droplets are dried in a dryer to form dry particles.

In a further aspect, the apparatus used to practice the present invention also includes a geometric particle sizer that determines a geometric diameter of the dry particles, and an aerodynamic particle sizer that determines an aerodynamic diameter of the dry particles.

Methods and apparatus suitable for forming particles of the present invention are discussed in U.S. Patent Application entitled "Method and Apparatus for Producing Dry Particles", filed concurrently herewith, which is a Continuation-in-part of U.S. patent application Ser. No. 10/101,563 entitled "Method and Apparatus for Producing Dry Particles", filed on Mar. 20, 2002. Methods and apparatus suitable for forming particles of the present invention are discussed in PCT Application filed concurrently herewith. The entire contents of these applications are incorporated herein by reference.

Spray drying solutions prepared as described above are fed to a drying vessel. For example, a nozzle or a rotary atomizer may be used to distribute the solutions to the drying vessel. In a preferred embodiment, a rotary atomizer is employed, such as a vaned rotary atomizer. For example, a rotary atomizer having a 4- or 24-vaned wheel may be used. An example of a suitable spray dryer using rotary atomization is the Mobile Minor Spray Dryer, manufactured by Niro, Inc. (Denmark).

Actual spray drying conditions will vary depending in part on the composition of the spray drying solution and material flow rates. In some embodiments, the inlet temperature to the spray dryer is about 100 to 200° C. In some embodiments, the inlet temperature is about 110 to 160° C.

The spray dryer outlet temperature will vary depending upon such factors as the feed temperature and the properties of the materials being dried. In one embodiment, the outlet temperature is about 35 to 80° C. In another embodiment, the outlet temperature is about 45 to 70° C., such as for example about 45 to 65° C. or about 60 to 70° C.

In one embodiment, the present invention is directed to a method for pulmonary delivery of a therapeutic, diagnostic or prophylactic agent, the method comprising administering an effective amount of particles to the respiratory tract of a person in need of treatment, prophylaxis or diagnosis. The particles of the invention can be used to provide controlled systemic or local delivery of therapeutic, prophylactic or diagnostic agents to the respiratory tract via aerosolization. Administration of the particles to the lung by aerosolization permits deep lung delivery of relatively large diameter therapeutic aerosols, for example, greater than about 3 microns or greater than about 5 microns in median diameter. Porous or aerodynamically light particles, having a geometric size (or mean diameter) in the range of about 5 to 30 microns, and tap density less than about 0.4 g/cm$^3$, such that they possess an aerodynamic diameter of about 1 to 3 microns, have been shown to display ideal properties for delivery to the deep lung. Larger aerodynamic diameters, ranging, for example, from about 3 to 5 microns are preferred, however, for delivery to the central and upper airways.

The particles can be fabricated with a rough surface texture to reduce particle agglomeration and improve flowability of the powder. The spray-dried particles have improved aerosolization properties. Spray-dried particles can be fabricated with features which enhance aerosolization via dry powder inhaler devices, and lead to decreased deposition in the mouth, throat and inhaler device.

The term "effective amount," as used herein, refers to the amount of agent needed to achieve the desired therapeutic, prophylactic or diagnostic effect or efficacy. The actual effective amounts of drug can vary according to the specific drug or combination thereof being utilized, the particular composition formulated, the mode of administration, and the age, weight, condition of the patient, and severity of the symptoms or condition being treated. Dosages for a particular patient can be determined by one of ordinary skill in the art using conventional considerations, for example, by means of an appropriate pharmacological protocol.

The particles of the invention can be employed in compositions suitable for drug delivery via the pulmonary system. For example, such compositions can include the particles and a pharmaceutically acceptable carrier for administration to a patient, preferably for administration via inhalation. The particles can be co-delivered with larger carrier particles, not including a therapeutic agent, the latter possessing mass median diameters for example in the range between about 50 and 100 microns. The particles can be administered alone or in any appropriate pharmaceutically acceptable carrier, such as a liquid, for example saline, or a powder, for administration to the respiratory system.

Particles, comprising suitable agents referred to above, are administered to the respiratory tract of a patient in need of treatment, prophylaxis or diagnosis. Administration of particles to the respiratory system can be by means such as those known in the art. For example, particles can be delivered from an inhalation device. In a preferred embodiment, particles are administered as a dry powder via a dry powder inhaler (DPI). Metered-dose-inhalers (MDI), nebulizers or instillation techniques also can be employed.

The methods of the invention also relate to administering to the respiratory tract of a subject, particles and/or compositions comprising the particles of the invention, which can be enclosed in a receptacle. As described herein, in certain embodiments, the invention is drawn to methods of delivering the particles of the invention, while in other embodiments, the invention is drawn to methods of delivering respirable compositions comprising the particles of the invention. As used herein, the term "receptacle" includes but is not limited to, for example, a capsule, blister, film covered container well, chamber and other suitable means of storing particles, a powder or a respirable composition in an inhalation device known to those skilled in the art.

In a preferred embodiment, the receptacle is used in a dry powder inhaler. Examples of dry powder inhalers that can be employed in the methods of the invention include but are not limited to, the inhalers disclosed is U.S. Pat. No. 4,995,385 and 4,069,819, Spinhaler (Fisons, Loughborough, U.K.), Rotahaler® (GlaxoSmithKline, Research Triangle Technology Park, N.C.), FlowCaps® (Hovione, Loures, Portugal), Inhalator® (Boehringer-Ingelheim, Germany), Aerolizer® (Novartis, Switzerland), Diskhaler (GlaxoSmithKline, RTP, NC), Diskus® (GlaxoSmithKline, RTP, NC) and others known to those skilled in the art. In one embodiment, the inhaler employed is described in U.S. patent application Ser. No. 09/835,302, entitled "Inhalation Device and Method," filed on Apr. 16, 2001. The entire contents of this application are incorporated herein by reference.

The invention is also drawn to receptacles which are capsules, for example, capsules designated with a particular capsule size, such as size 2. Suitable capsules can be obtained, for example, from Shionogi (Rockville, Md.). The invention is also drawn to receptacles which are blisters. Blisters can be obtained, for example, from Hueck Foils, (Wall, N.J.). Other receptacles and other volumes thereof suitable for use in the present invention are known to those skilled in the art.

The receptacle encloses or stores particles and/or respirable compositions comprising particles. In one embodiment, the particles and/or respirable compositions comprising particles are in the form of a powder. The receptacle is filled with particles and/or compositions comprising particles, as known in the art. For example, vacuum filling or tamping technologies may be used. Generally, filling the receptacle with powder can be carried out by methods known in the art. In one embodiment of the invention, the particles, powder or respirable composition which is enclosed or stored in a receptacle has a mass of at least about 1.0 mg. In another embodiment, the mass of the particles or respirable compositions stored or enclosed in the receptacle is at least about 5.0 mg. Alternatively about 1 to 10 milligrams or about 1 to 5 milligrams are stored or enclosed. In yet another embodiment, the mass of the particles or respirable compositions stored or enclosed in the receptacle is up to about 20, 25, 30, or 50 milligrams. The receptacle and the inhalers are used in the recommended temperature range of about 5 to 35° C. and at about 15 to 85% relative humidity.

In one embodiment of the invention, the receptacle encloses a mass of particles, especially a mass of highly dispersible particles as described herein. The mass of particles comprises a nominal dose of an agent. As used herein, the phrase "nominal dose" means the total mass of an agent which is present in the mass of particles in the receptacle and represents the maximum amount of agent available for administration in a single breath.

Particles and/or respirable compositions comprising particles are stored or enclosed in the receptacles and are administered to the respiratory tract of a subject. As used herein, the terms "administration" or "administering" of particles and/or respirable compositions refer to introducing particles to the respiratory tract of a subject.

As described herein, in one embodiment, the invention is drawn to a respirable composition comprising carrier particles and an agent. In another embodiment, the invention is drawn to a method of delivering a respirable composition comprising carrier particles and an agent. As used herein, the term "carrier particle" refers to particles which may or may not comprise an agent, and aid in delivery of an agent to a subject's respiratory system, for example, by increasing the stability, dispersibility, aerosolization, consistency and/or bulking characteristics of an agent. It is clear that in certain embodiments, the particles of the invention are carrier particles which are capable of being delivered to the respiratory tract of a subject.

It is understood that the particles and/or respirable compositions comprising the particles of the invention which can be administered to the respiratory tract of a subject can also optionally include pharmaceutically-acceptable carriers, as are well known in the art. The term "pharmaceutically-acceptable carrier" as used herein, refers to a carrier which can be administered to a patient's respiratory system without any significant adverse toxicological effects. Appropriate pharmaceutically-acceptable carriers, include those typically used for inhalation therapy (e.g., lactose) and include pharmaceutically-acceptable carriers in the form of a liquid (e.g., saline) or a powder (e.g., a particulate powder). In one embodiment, the pharmaceutically-acceptable carrier comprises particles which have a mean diameter ranging from about 50 to 200 microns, and in particular lactose particles in this range. It is understood that those of skill in the art can readily determine appropriate pharmaceutically-acceptable carriers for use in administering, accompanying and or co-delivering the particles of the invention.

In one embodiment of the invention, the particles and/or respirable compositions comprising particles, are administered in a single, breath-activated step. As used herein, the phrases "breath-activated" and "breath-actuated" are used interchangeably. As used herein, "a single, breath-activated step" means that particles are dispersed and inhaled in one step. For example, in single, breath-activated inhalation devices, the energy of the subject's inhalation both disperses particles and draws them into the oral or nasopharyngeal cavity. Suitable inhalers which are single, breath-actuated inhalers that can be employed in the methods of the invention include but are not limited to simple, dry powder inhalers disclosed in U.S. Pat. Nos. 4,995,385 and 4,069,819, Spinhaler® (Fisons, Loughborough, U.K.), Rotahaler® (GlaxoSmithKline, Research Triangle Technology Park, N.C.), FlowCaps® (Hovione, Loures, Portugal), Inhalator® (Boehringer-Ingelheim, Germany), Aerolizer® (Novartis, Switzerland), Diskhaler (GlaxoSmithKline, RTP, N.C.), Diskus® (GlaxoSmithKline, RTP, N.C.) and others, such as known to those skilled in the art. In one embodiment, the inhaler employed is described in U.S. patent application Ser. No. 09/835,302, entitled "Inhalation Device and Method," filed on Apr. 16, 2001. The entire contents of this application are incorporated by reference herein.

"Single breath" administration can include not only single, breath-activated administration, but also administration during which the particles, respirable compositions or powders are first dispersed, followed by the inhalation or inspiration of the dispersed particles, respirable compositions or powders. In the latter mode of administration, additional energy other than the energy supplied by the subject's inhalation disperses the particles. An example of a single breath inhaler which employs energy other than the energy generated by the patient's inhalation is the device described in U.S. Pat. No. 5,997,848 issued to Patton, et al., on Dec. 7, 1999, the entire teachings of which are incorporated herein by reference.

In one embodiment, the receptacle enclosing the particles, respirable compositions comprising particles or powder is emptied in a single, breath-activated step. In another embodiment, the receptacle enclosing the particles is emptied in a single inhalation. As used herein, the term "emptied" means that at least 50% of the particle mass enclosed in the receptacle is emitted from the inhaler during administration of the particles to a subject's respiratory system. This is also called an "emitted dose." The mass of an emitted dose will vary depending on the delivery system used. In one embodiment, the emitted dose will range from about 50 to 95% of the particle mass enclosed in the receptacle. Alternatively, greater than 50%, 60%, 70%, 80%, or 90% of the particle mass enclosed in the receptacle is emitted.

Delivery to the pulmonary system of particles in a single, breath-actuated step is enhanced by employing particles which are dispersed at relatively low energies such as, for example, at energies typically supplied by a subject's inhalation. Such energies are referred to herein as "low." As used herein, "low energy administration" refers to administration wherein the energy applied to disperse and inhale the particles is in the range typically supplied by a subject during inhaling.

One method for delivering an agent to the pulmonary system is described in U.S. patent application Ser. No. 09/878,146, entitled "Highly Efficient Delivery of a Large Therapeutic Mass Aerosol," filed on Jun. 8, 2001, the contents of which are incorporated herein in their entirety.

In a preferred embodiment of the invention, the particles administered are highly dispersible. As used herein, the phrase "highly dispersible" particles or powders refers to particles or powders which can be dispersed by a RODOS dry powder disperser (or equivalent technique) such that at about 1 bar, particles of the dry powder emit from the RODOS orifice with geometric diameters, as measured by a HELOS or other laser diffraction system, that are less than about 1.5 times the geometric particle size as measured at 4 bar. Highly dispersible powders have a low tendency to agglomerate, aggregate or clump together and/or, if agglomerated, aggregated or clumped together, are easily dispersed or de-agglomerated as they emit from an inhaler and are breathed in by the subject. Typically, the highly dispersible particles suitable in the methods of the invention display very low aggregation compared to standard micronized powders which have similar aerodynamic diameters and which are suitable for delivery to the pulmonary system. Properties that enhance dispersibility include, for example, particle charge, surface roughness, surface chemistry and relatively large geometric diameters. In one embodiment, because the attractive forces between particles of a powder varies (for constant powder mass) inversely with the square of the geometric diameter and the shear force seen by a particle increases with the square of the geometric diameter, the ease of dispersibility of a powder is on the order of the inverse of the geometric diameter raised to the fourth power. The increased particle size diminishes interparticle adhesion forces. (Visser, J., *Powder Technology,* 58:1-10 (1989)). Thus, large particle size, all other things equivalent, increases efficiency of aerosolization to the lungs for particles of low envelope mass density. Increased surface irregularities, and roughness also can enhance particle dispersibility. Surface roughness can be expressed, for example, by rugosity.

Particles suitable for use in the methods of the invention can travel through the upper airways (for example, oropharynx and larynx), the lower airways, which include the trachea followed by bifurcations into the bronchi and bronchioli and through the terminal bronchioli which in turn divide into respiratory bronchioli leading then to the ultimate respiratory zone, the alveoli or the deep lung. In one embodiment of the invention, most of the mass of particles deposit in the deep lung. In another embodiment of the invention, delivery is primarily to the central airways. In another embodiment, delivery is to the upper airways.

In one aspect particles comprising ipratropium bromide and salmeterol xinafoate are administered to a patient for the treatment, prophylaxis or diagnosis of a lung disorder such as, for example, a condition associated with reversible airways obstruction. In one embodiment, particles are administered for the treatment, prophylaxis or diagnosis of chronic obstructive pulmonary disease (COPD), including, but not limited to, emphysema or chronic bronchitis. In another embodiment, particles are administered for the treatment, prophylaxis or diagnosis of asthma or an asthma related disorder.

The term "dose" of agent refers to that amount that provides therapeutic, prophylactic or diagnostic effect in an administration regimen. A dose may consist of more than one actuation of an inhaler device. The number of actuations of an inhaler device by a patient are not critical to the invention and may be varied by the physician supervising the administration.

Aerosol dosage, formulations and delivery systems may be selected for a particular therapeutic application, as described, for example, in Gonda, 1. "Aerosols for delivery of therapeutic and diagnostic agents to the respiratory tract," in *Critical Reviews in Therapeutic Drug Carrier Systems*, 6: 273-313, 1990; and in Moren, "Aerosol dosage forms and formulations," in: *Aerosols in Medicine. Principles, Diagnosis and Therapy*, Moren, et al., Eds, Esevier, Amsterdam, 1985.

EXEMPLIFICATION

For Examples 1 through 5, formulations A through D are in Tables 1 through 4.

EXAMPLE 1

Particle Production

Particle formulations, as listed in Table 1, where prepared by spray drying. Pre-spray drying solutions were prepared as follows. Particle components were dissolved in appropriate solvents to assure solubility. Table 2 lists the mass of each particle component dissolved in each respective solvent. Leucine and sucrose, if present, were dissolved in 300 mL of water. Albuterol sulfate was subsequently dissolved in the aqueous solution. DPPC and/or DSPC were dissolved in 700 mL of ethanol. Both solutions were then heated separately to 50° C. The aqueous phase was then mixed into the organic phase to form a pre-spray drying solution with a total volume of about IL and a dissolved solids concentration of 1 g/L. These co-solvent mixtures were clear at 50° C.

Phospholipids were obtained from Avanti Polar Lipids, Inc. (Alabaster, Ala.). Albuterol sulfate and leucine were obtained from Spectrum Quality Products, Inc. (Gardena, Calif.).

The solution was then spray dried to produce dry powders. A Niro Atomizer Portable Spray Dryer (Niro, Inc., Columbus, Md.) was used. Compressed air with variable pressure (1 to 5 bar) drove a 4-vaned rotary atomizer, spinning at about 47,000 rpm, located above the dryer. Liquid feed at a rate of 70 mL/min was pumped continuously by a peristaltic pump to the atomizer. Dry nitrogen gas was used as the drying medium. Both the inlet and outlet temperatures were measured. The inlet temperature was controlled manually and was established at approximately 110° C. Outlet temperature is determined by such factors as the input temperature and the gas and liquid feed rates, among others. The outlet temperature generally varied between about 44 and 48° C. A container was tightly attached to a cyclone for collecting the powder product.

TABLE 1

Example Formulations

| Formulation | Composition (weight percent) |
|---|---|
| A | Leucine (46%); DPPC (46%); Albuterol Sulfate (8%) |
| B | Leucine (16%); DPPC (36%); DSPC (38%); Albuterol Sulfate (8%) |
| C | Leucine (16%); DPPC (76%); Albuterol Sulfate (8%) |
| D | Leucine (76%); Sucrose (16%); Albuterol Sulfate (8%) |

TABLE 2

Pre-Spray Drying Solution Composition

| | Ethanol Solution Components | | Aqueous Solution Components | | |
|---|---|---|---|---|---|
| Formulation | DPPC | DSPC | Leucine | Albuterol Sulfate | Sucrose |
| A | 460 mg | — | 460 mg | 80 mg | — |
| B | 380 mg | 380 mg | 160 mg | 80 mg | — |
| C | 760 mg | — | 160 mg | 80 mg | — |
| D | — | — | 760 mg | 80 mg | 160 mg |

EXAMPLE 2

The mass median aerodynamic diameter, volumetric median geometric diameter, and tap density of the particles produced in Example 1 were determined.

The mass median aerodynamic diameter (MMAD) of the particles was determined using an Aerosizer/Aerodisperser (Amherst Process Instrument, Amherst, Mass.). Approximately 2 mg of powder formulation was introduced into the Aerodisperser and the aerodynamic size was determined by time of flight measurements.

The volumetric median geometric diameter (VMGD) of the particles was measured using a RODOS dry powder disperser (Sympatec, Princeton, N.J.) in conjunction with a HELOS laser diffractometer (Sympatec). Powder was introduced into the RODOS inlet and aerosolized by shear forces generated by a compressed air stream regulated at 2 bar. The aerosol cloud was subsequently drawn into the measuring zone of the HELOS, where it scattered light from a laser beam and produced a Fraunhofer diffraction pattern used to infer the particle size distribution and determine the median value.

Mass median aerodynamic diameter, volumetric median geometric diameter, and tap density for each of the formulations produced in Example 1 are shown in Table 3 below. The powders produced are respirable, as indicated by the physical characteristics of the powders shown in Table 3.

TABLE 3

Particle Characterization Data

| Formulation | VGMD (microns) | MMAD (microns) | Tap Density (g/cm$^3$) |
|---|---|---|---|
| A | 7.89 | 2.19 | 0.077 |
| B | 5.77 | 2.01 | 0.121 |
| C | 11.96 | 2.64 | 0.049 |
| D | 7.76 | 2.37 | 0.093 |

EXAMPLE 3

Powders having compositions as in Table 1 Formulations A, B and D were prepared by the method of Example 1. These particles were then tested for protection from bronchoconstriction following bronchoprovocative methacoline challenge in a guinea pig model of airway hyperresponsiveness.

Young adult male Hartley guinea pigs were obtained from ElmHill Breeding Laboratories, Inc. (Chemsford, Mass.). At the time of use, the animals weighed between 330 and 393 g (mean weight was 351±5 g (S.E.M.)).

A nominal dose of 25 micrograms albuterol sulfate was delivered to the animals by intratracheally dosing with 312 micrograms of dry powder. Four animals were dosed with each of the three powder formulations (i.e., n=4 per powder).

The powder was delivered to the lungs of anesthetized animals by an insufflation technique using a Penn-Century insufflation device (Philadelphia, Pa.). Animals were randomly selected from the test population for each treatment. Using a laryngoscope, the delivery tube of the insufflator was inserted through the oropharynx and into the trachea until the tip of the tube was about a centimeter from the carina (first bifurcation). A 3 mL bolus was used to activate the Penn-Century devices and deliver the powder from the dosing barrel. This bolus of air was repeated three times for a total of three discharges per powder dose in order to decrease or eliminate powder residues in the sample chamber. Animals were then returned to their cages and observed until recovery from anesthesia; subsequently, bronchoprotection was assessed.

A BUXCO Unrestrained Whole-Body Plethysmography System (BUXCO Electronics, Inc., Sharon, Conn.) was used with customized software to assess pulmonary function changes. Airway hyperresponsiveness in normal animals to nebulized methacholine (750 µg/mL solubilized in saline; Sigma Chemical Company, St. Louis, Mo.) was assessed using the BUXCO system both prior to dosing (i.e., as an assessment of baseline airway hyperresponsiveness) and also at 2, 6, 10 and 24 hours following particle administration. The enhanced pause value (PenH), a flow-based indicator of airway resistance, was used as an indicator of bronchoprotection. A significant increase in this value indicated significant bronchoconstriction, while prevention of this increase in response to methacholine indicated bronchoprotection.

FIG. 1 shows the results of in vivo guinea pig testing of three dry powder formulations containing varying amounts of leucine and phospholipids and 8 weight percent albuterol sulfate. Surprisingly, Formulation A, containing 46 weight percent each of leucine and DPPC, demonstrated a prolonged bronchoprotection with the lowest enhanced pause (PenH) value recorded at 6 hours following treatment.

Formulations B, containing 16 weight percent leucine and 76 weight percent phospholipids, and D, containing 76 weight percent leucine and 16 weight percent sucrose, exhibited shorter durations of bronchoprotection, and by 6 hours post-treatment, their respective PenH values were higher than those of Formulation A.

Thus, the data demonstrate that particles containing a combination of phospholipid with a sufficient amount of leucine, such as at least 46 weight percent of leucine, possess enhanced controlled release characteristics and also that a significant fraction of leucine, where the other excipient is sucrose, does not lead to controlled release of albuterol (i.e., as compared to particles containing phospholipids).

EXAMPLE 4

Powders having compositions of Table 1 formulations A, B and D were prepared by the method of Example 1. These particles were then evaluated in vivo for pharmacokinetic profiles.

Male Sprague-Dawley rats were obtained from Taconic Farms (Germantown, N.Y.). At the time of use, the animals weighed 317 g on average (+6 g S.E.M.).

A nominal dose of 25 micrograms albuterol sulfate was delivered to the rats by intratracheally dosing with 312 micrograms of dry powder. Five to six rats were dosed with each of the three powder formulations (i.e., n=5-6 per powder).

The powders were delivered to the lungs using an insufflator device for rats (PennCentury, Philadelphia, Pa.). The powder amount was transferred into the insufflator sample chamber. The delivery tube of the insufflator was then inserted through the mouth into the trachea and advanced until the tip of the tube was about a centimeter from the carina (first bifurcation). The volume of air used to deliver the powder from the insufflator sample chamber was 3 mL, delivered from a 10 mL syringe. In order to maximize powder delivery to the rat, the syringe was recharged and discharged two more times for a total of three air discharges per powder dose.

Catheters were placed into the jugular veins of the rats the day prior to dosing. At sampling times, blood samples were drawn from the jugular vein catheters. Sampling was preformed prior to dosing (pre-dose) and also at 0.25, 0.5, 1, 2, 4, 6 and 8 hours post-dose. Plasma was then analyzed for albuterol concentration by Enzyme-Linked Immuno-Sorbent Assay (ELISA) (Neogen Corp., Lexington, Ky.).

Figure 2:
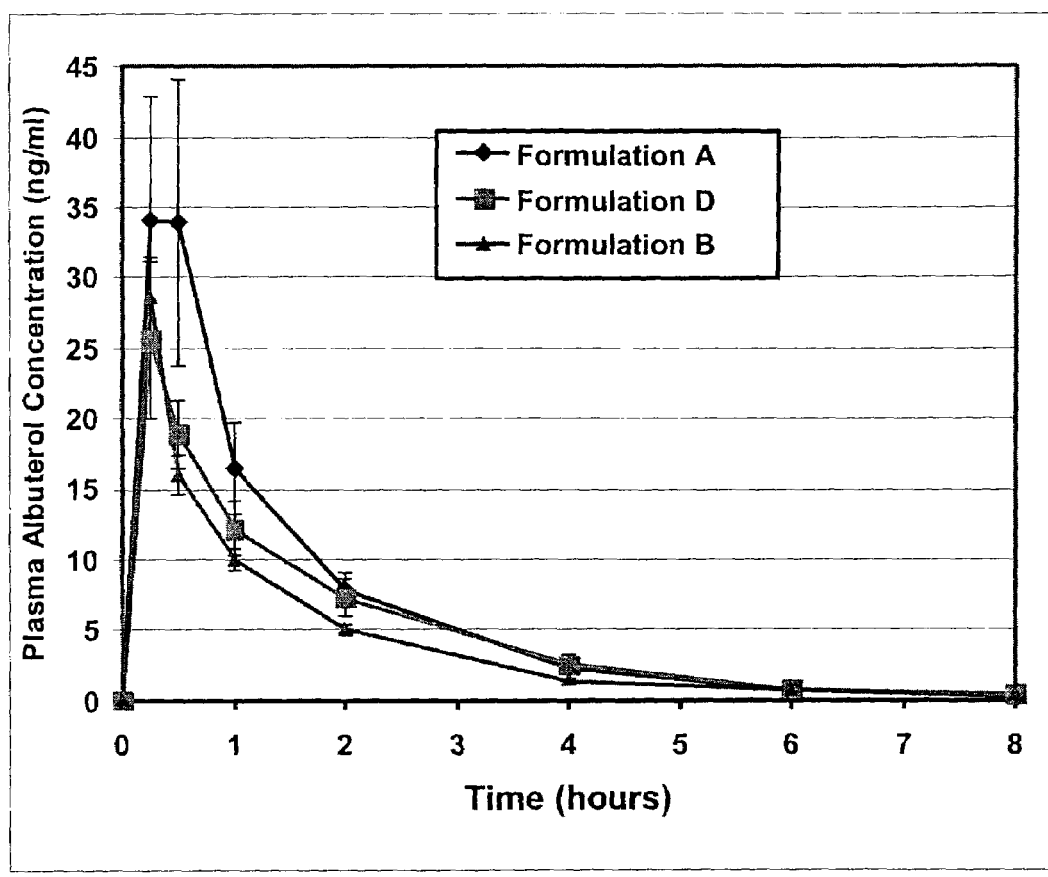

Plasma albuterol concentrations over time for each of the formulations are shown in FIG. 2. Table 4 contains areas under the curve (AUC) calculated from the data of FIG. 2; maximum plasma albuterol concentration, $C_{max}$; and time to maximum plasma albuterol concentration, $T_{max}$. Higher AUC and/or higher $T_{max}$ indicate sustained release of albuterol.

TABLE 4

| Area Under the Plasma Albuterol Concentration vs. Time Curve of FIG. 2 | | | |
|---|---|---|---|
| Formulation | Area under the Curve | $T_{MAX}$(min) | $C_{MAX}$(ng/mL) |
| A | 51.5 ± 11.8 | 35 | 36.6 ± 10.8 |
| B | 32.7 ± 2.0 | 25 | 28.6 ± 28 |
| D | 40.5 ± 8.7 | 25 | 25.6 ± 6.2 |

The data of FIG. 2 and Table 4 demonstrate (1) that particles containing a combination of phospholipid with a sufficient amount of leucine, such as at least 46 weight percent of leucine, possess enhanced controlled release characteristics and (2) that a significant fraction of leucine, when the other component is sucrose instead of phospholipid, does not lead to controlled release.

EXAMPLE 5

Powders having compositions as in Table 1 formulations A, C and D were prepared by the method of Example 1. These particles were then tested for reduction of mass mean diameter in isotone solution to determine the influence of composition on the physical integrity of the particles under fully hydrated conditions.

Approximately 1 milligram of particles were dispersed in about 20 mL isotone solution at 37° C. A Multisizer 3 Coulter Counter (Beckman Coulter, Inc., Fullerton, Calif.) was used to measure the particle size distribution at several timepoints. The percent reduction of particle initial mass median diameter over time is shown in FIG. 3.

Figure 3:
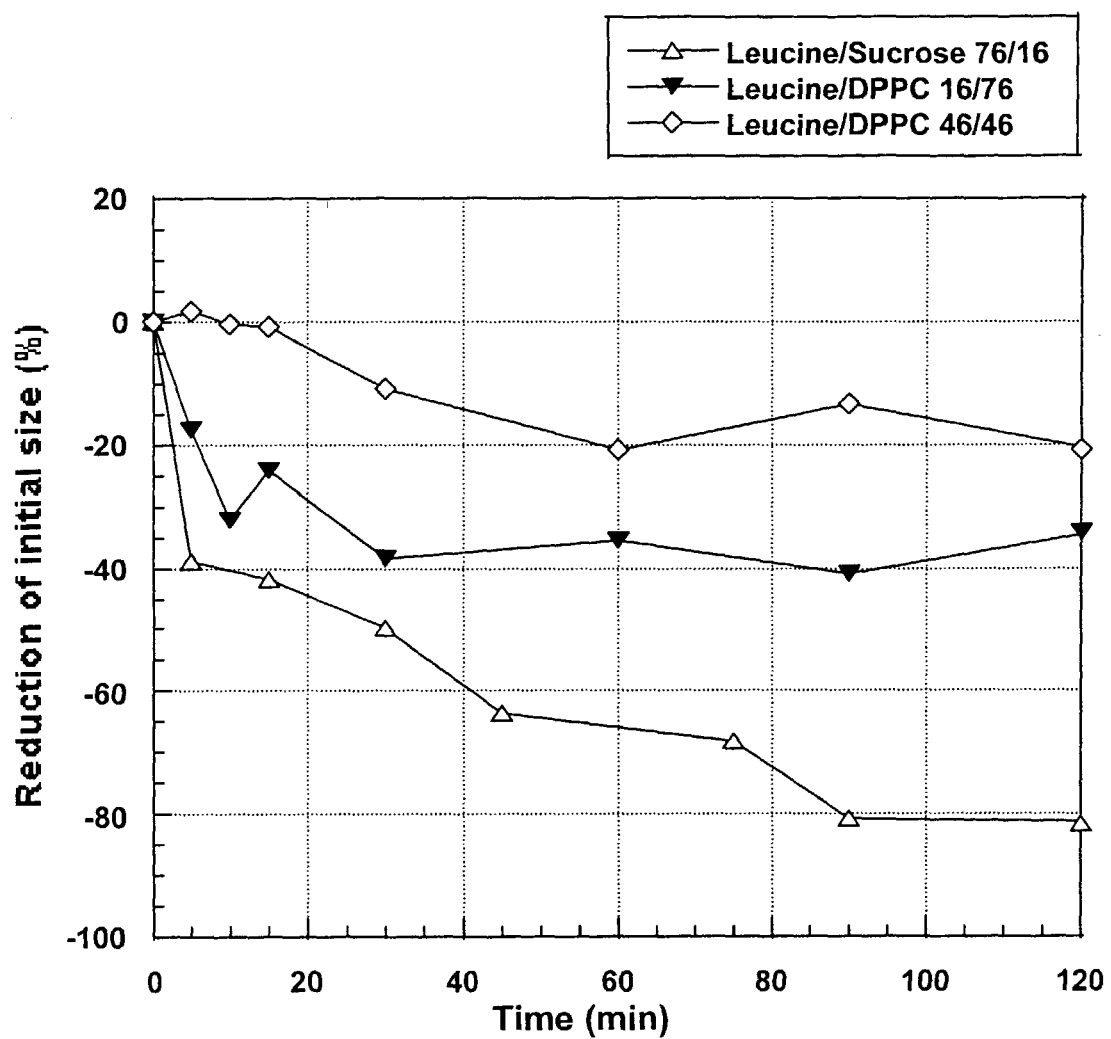
Figure 4:
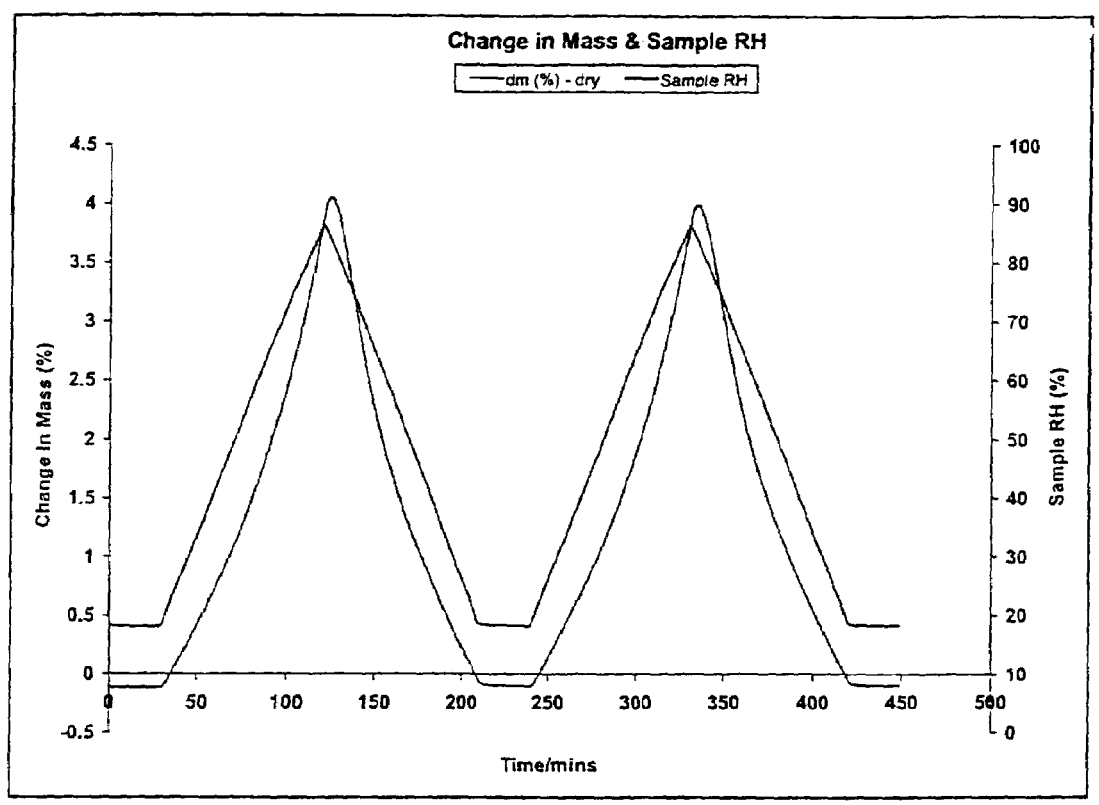
Figure 5:
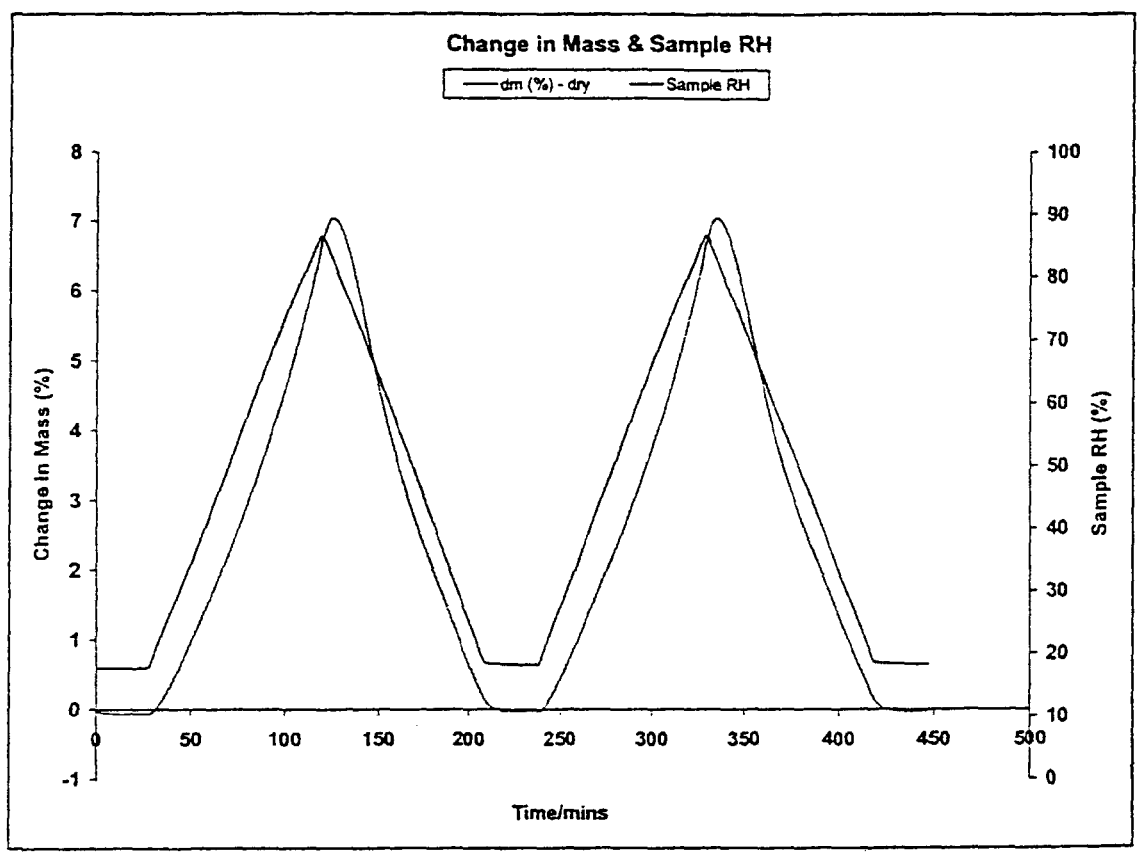
Figure 6:
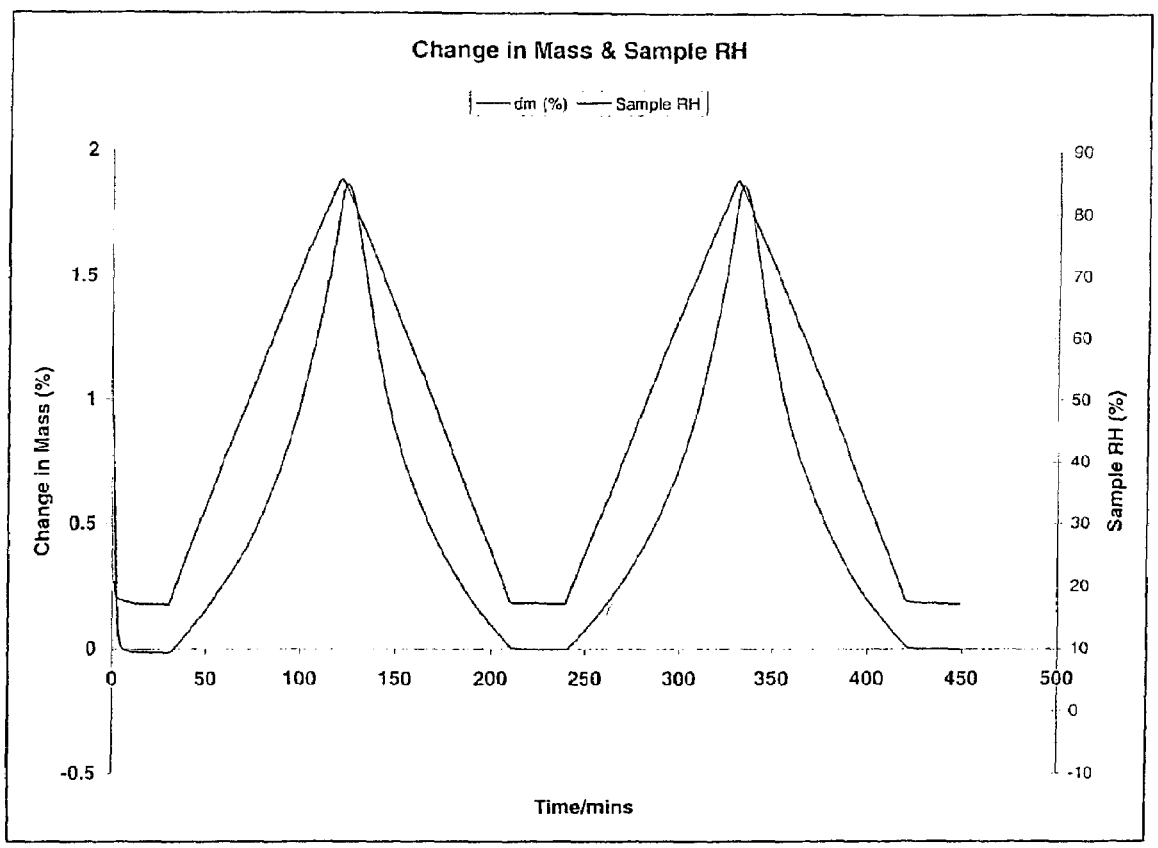
Figure 7:
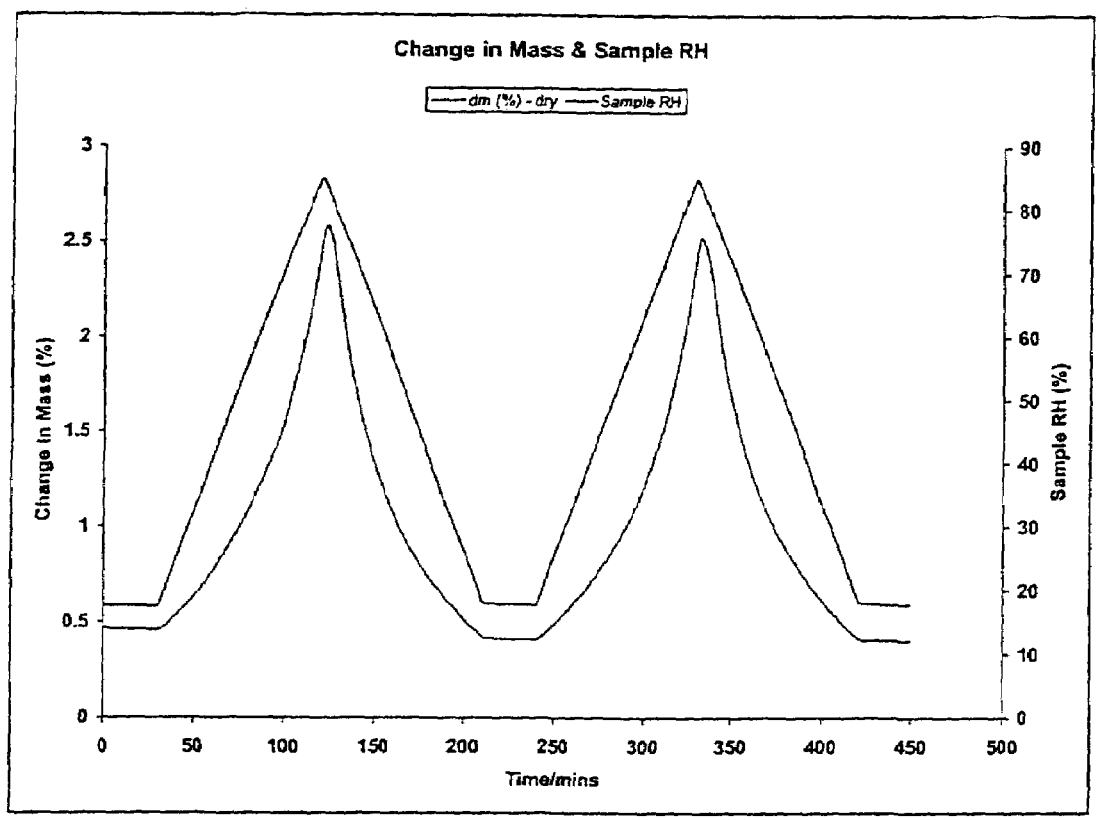
Figure 8:
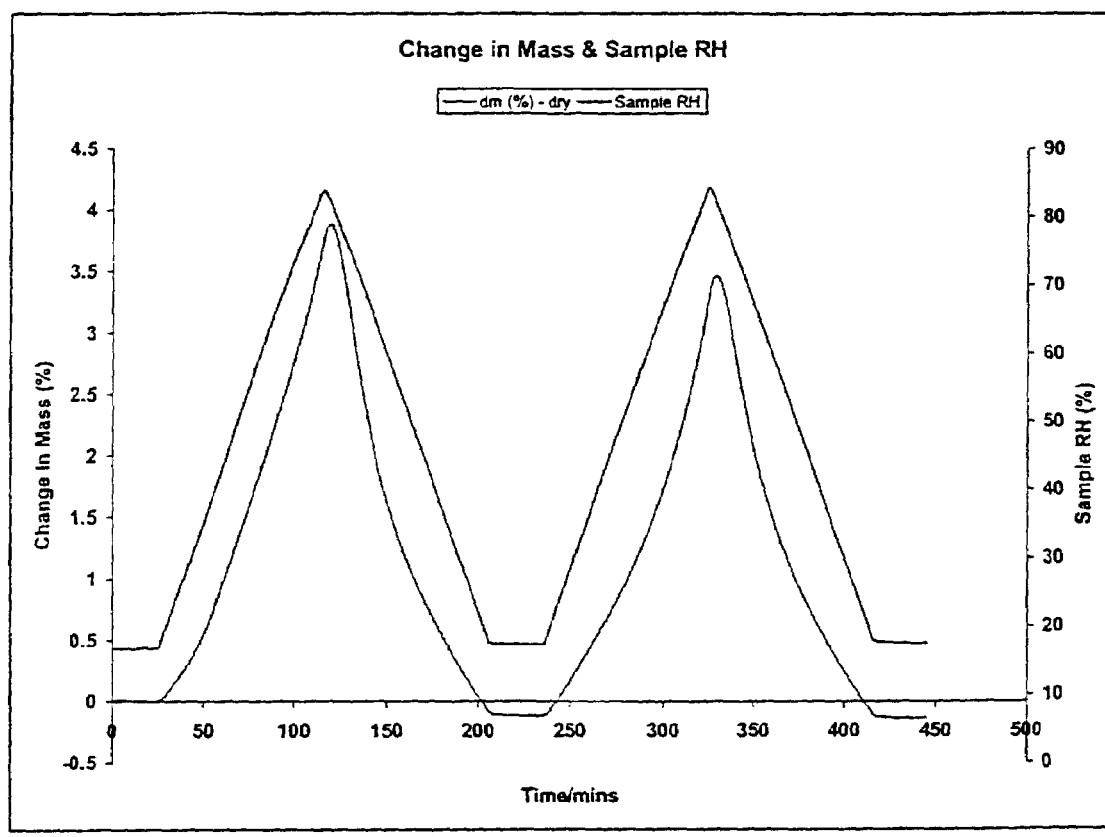

As shown in FIG. 3, particles containing phospholipids and leucine can undergo different kinetic of size reduction according to their composition. Unexpectedly, the particles of Formulation A, containing 46 weight percent each of leucine and DPPC, showed a more controlled and gradual reduction of their size as compared to the particles of Formulation C, containing 16 weight percent leucine and 76 weight percent DPPC. The particles of Formulation D, containing 76 weight percent leucine and 16 weight percent sucrose, exhibited the most dramatic size reduction over the duration of the experiment.

For Examples 6-12 below, the formulations A through K comprise ipratropium bromide and salmeterol xinafoate as shown in Tables I though IX. Particles for pulmonary delivery of ipratropium bromide and salmeterol xinafoate were produced to identify those formulations that maximized chemical, physical and solid state stability while maintaining desired pulmonary bioavailability of these agents. Particles were evaluated in three sequential tiers of testing, with a reduction in the number of formulations tested at each level. Formulations were passed through a selection process based upon relative performance within each level of testing. Table I shows five formulations that maximize chemical, physical and solid state stability while maintaining desired pulmonary bioavailability.

Note that formulation designations (e.g., A, B, etc.) are used consistently throughout the Exemplification to designate the same particle compositions.

TABLE I

Five Formulations Exhibiting Maximized Chemical, Physical and Solid State Stability

| Formulation | Formulation Class | Composition |
|---|---|---|
| A | III | DPPC (10%); DSPC (10%); Leucine (68%); Ipratropium Bromide (5%); Salmeterol Xinafoate (7%) |
| B | V | DPPC (12%); DSPG(35%); Leucine (41%); Ipratropium Bromide (5%); Salmeterol Xinafoate (7%) |
| C | VII | Leucine (88%); Ipratropium Bromide (5%); Salmeterol Xinafoate (7%) |
| D | VII | Leucine (80%); Mannitol (8%); Ipratropium Bromide (5%); Salmeterol Xinafoate (7%) |
| E | IV | MSPC (12%); DMPE (37%); Leucine (39%); Ipratropium Bromide (5%); Salmeterol Xinafoate (7%) |

All percentages are (wt/wt total solids).

EXAMPLE 6

Particle (Powder) Production Ipratropium bromide (IpBr), salmeterol xinafoate (SX), and selected excipients were dissolved into water, ethanol or a water/ethanol mixture. Solvents were selected to optimize solubility of the formulation components. Generally, ethanol soluble components (e.g., DPPC, MSPC, and salmeterol xinafoate) were dissolved into ethanol and the solution was heated as necessary for solubilization (e.g. to about 40 to 50° C.). Water soluble components (e.g., leucine, mannitol, sodium citrate, calcium chloride, and ipratropium bromide) were dissolved in water. Aqueous solutions containing sodium citrate and calcium chloride were buffered to approximately a pH of approximately 7.0. Immediately prior to spray drying, pre-spray drying solutions were formed by mixing the ethanol solution and the aqueous solution. The solutions were combined at 30:70 (v/v) ethanol solution to water solution for non-phospholipid containing solutions and at either 60:40 or 70:30 (v/v) ethanol solution to water solution for phospholipid containing solutions. The ethanol/water pre-spray drying solutions contained about 1 gram of dissolved solids per liter of total solution. These solutions were maintained between 20-50° C. (as needed to assure solubility) prior to powder production.

Solution formulations were grouped into 9 classes as shown in Table II. Each formulation contained lipids and/or excipients selected from among those shown in Table II. Each of the formulations represented either a unique combination of materials o r a unique proportion of materials.

TABLE II

Formulation Classes with Possible Lipid and Excipient Compositions

| Class | Lipids | Excipients |
|---|---|---|
| I | DPPC, DSPC | Sodium Citrate*, Calcium Chloride*, Leucine |
| II | DPPC, DSPC, DMPE, DPPE | Lactose, Leucine |
| III | DPPC, DSPC | Trehalose, Leucine* |
| IV | MSPC*, DSPC, DMPE | Leucine* |
| V | DPPC, DSPC, DPPE, DMPE + (DSPG or DPPG)* | Calcium Chloride, Leucine |
| VI | DPPC, DSPC, DMPE | Precirol*, Leucine* |
| VII | None | Sugars, Polyethylene Glycol, Leucine* |
| VIII | DPPC, DMPE, DSPG | Maltodextrin* |
| IX | DPPC* + DSPC* | None |

*Material used in each formulation of its respective class.

The concentrations of ipratropium bromide and salmeterol xinafoate were kept constant at 5% and 7%(w/w total solids), respectively, in each formulation of classes I-VIII. The formulations of class IX were produced having varied salmeterol xinafoate and ipratropium bromide loading; specifically, salmeterol xinafoate loading of about 4 to 7% (w/w total solids) and ipratropium bromide loading of about 4 to 13% (w/w total solids) were examined.

The solutions as prepared above were spray dried using a Mobile Minor Spray Dryer (Niro, Inc., Columbus, Md.). Two different rotary atomizers were used to produce droplets. Either a 4- or 24-vaned atomizer wheel, spinning at about 34,000 to 48,000 rpm, was used to distribute the solutions to the dryer. The solution feed rate was about 60 to 75 mL per minute. The spray dryer inlet temperatures were between 110 and 160° C. Outlet temperatures were between 45 and 55° C.

Powders were collected in a cyclone trapping system. Prior to analysis, all powders were stored under controlled temperature and humidity conditions (i.e., 23° C. and 15% Relative Humidity).

Table m shows six powder formulations prepared for comparison with the performance of the formulations of Table I.

TABLE III

Six IpBr/SX Formulations for Comparative Analysis

| Formulation | Formulation Class | Composition |
|---|---|---|
| F | II | DMPE (44%); Leucine (44%); Ipratropium Bromide (5%); Salmeterol Xinafoate (7%) |
| G | IV | MSPC (24.5%); DSPC(24.5%); Leucine (39%); Ipratropium Bromide (5%); Salmeterol Xinafoate (7%) |
| H | VIII | Leucine (63%); Maltodextrin M100 (15%); DMPE (10%); Ipratropium Bromide (5%); Salmeterol Xinafoate (7%) |

TABLE III-continued

Six IpBr/SX Formulations for Comparative Analysis

| Formulation | Formulation Class | Composition |
|---|---|---|
| I | V | DPPE (24%); DSPG (24%); Leucine (40%); Ipratropium Bromide (5%); Salmeterol Xinafoate (7%) |
| J | III | DSPC (55%); Leucine (33%); Ipratropium Bromide (5%); Salmeterol Xinafoate (7%) |
| K | II | DPPE (11%); DMPE (33%); Leucine (44%); Ipratropium Bromide (5%); Salmeterol Xinafoate (7%) |

All percentages are (wt/wt total solids).

EXAMPLE 7

The particles of Example 6 were evaluated for aerosol performance in the first tier of testing. Aerodynamically light particles can provide more effective delivery of a therapeutic agent to the pulmonary system than can conventional particles. Aerodynamically light particles can include those that have a mean diameter between about 5 and 30 microns and an aerodynamic diameter of between about 1 and 5 microns. Each of the formulations was evaluated for aerosol performance based on volumetric mean geometric diameter (VMGD), mass mean aerodynamic diameter (MMAD), and fine particle fraction (FPF).

a) Geometric Diameter

The volumetric mean geometric diameter (VMGD) of each powder was determined at two shear conditions, i.e., at 1 bar and at 2 bar, using a low-angle laser light scattering system variable-shearing disperser. A HELOS laser diffractometer in conjunction with a RODOS dry powder disperser, both manufactured by Sympatec Inc. (Princeton, N.J.) was used to measure VMGD. Powder was introduced into the RODOS inlet and aerosolized by shear forces generated by a compressed air stream regulated at a specified pressure (1 or 2 bar). The aerosol cloud was subsequently drawn into the measuring zone of the HELOS, where it scattered light from a laser beam and produced a Fraunhofer diffraction pattern used to infer the particle size distribution and determine the mean geometric diameter.

The formulations had measured VMGD of between 4.7 and 27.3 microns. All of the formulations had VMGD, measured at 1 bar, between 5.3 and 27.3 microns. All but two of the formulations had VMGD, measured at 2 bar, between 5.1 and 19.2 microns;

b) Aerodynamic Diameter

The mass mean aerodynamic diameter (MMAD) was determined using an Aerosizer DSP Model 3225 Particle Size Analyzer (Amherst Process Instrument, Inc., Amherst, Mass.) Approximately 2 mg of powder was placed into the dispersion cup for introduction to the Aerosizer. The Aerosizer then used time-of-flight measurements to determine aerodynamic diameter of the powder particles. Particle density was assumed to be an arbitrary 1 g/cm$^3$, but only for the purposes of these measurements.

The formulations had measured MMAD of between 2.3 and 5.4 microns. All but one of the formulations had measured MMAD between 2.3 and 4.1 microns.

c) Fine Particle Fraction

Fine Particle Fraction (FPF) was measured using a reduced Therno Anderson Cascade Impactor with two stages. Ten milligrams of powder was weighed into a size 2 hydroxpropyl methyl cellulose (HPMC) capsule. The powders were dispersed using a single-step, breath-actuated dry powder inhaler operated at 60 L/min for 2 seconds. The stages were selected to collect particles of an effective cutoff diameter (ECD) of (1) between 5.6 microns and 3.4 microns and (2) less than 3.4 microns and were fitted with porous filter material to collect the powder deposited. The mass deposited on each stage was determined gravimetrically. Three replicate runs were performed for each sample and the values were averaged. FPF was then expressed as a fraction of the total mass loaded into the capsule.

Each of the particle formulations had measured FPF (<5.6) between 0.22 and 0.71 and FPF (<3.4) between 0.10 and 0.41.

Volumetric mean geometric diameter, mass mean aerodynamic diameter, and fine particle fraction for the five formulations of Table I are shown in Table IV below.

TABLE IV

Aerosol Performance of Selected Particle Formulations

| Formulation | VMGD (at 1 bar shear) (μm) | VMGD (at 2 bar shear) (μm) | MMAD (μm) | FPF (<5.6 μm) | FPF (<3.4 μm) |
|---|---|---|---|---|---|
| A | 7.23 | 6.35 | 2.57 | 0.71 | 0.30 |
| B | 7.83 | 6.94 | 3.11 | 0.56 | 0.20 |
| C | 6.45 | 5.88 | 2.78 | 0.58 | 0.23 |
| D | 6.38 | 6.09 | 2.64 | 0.63 | 0.30 |
| E | 8.78 | 6.85 | 2.96 | 0.66 | 0.30 |

EXAMPLE 8

The powder formulations of Example 6 were also evaluated in the first tier of testing for solid state stability as an indicator of physical stability. The solid state structure was probed using dynamic vapor sorption (DVS) and differential scanning calorimetry (DSC).

a) Dynamic Vapor Sorption

Dynamic Vapor Sorption was employed to determine water uptake characteristics of the powder formulations. A DVS-1000 instrument from Surface Measurement Systems (London, United Kingdom) was used for all vapor sorption experiments. All experiments used 200 sccm of gas flow. Temperature was kept constant at 25° C. Approximately 10 to 15 mg of powder was used for each experiment. The experiments were conducted in dual ramp mode using the following protocol:

Step 1—hold the powder at 20% relative humidity (RH) for 0.5 hours

Step 2—ramp the humidity up to 90% RH over 1.5 hours

Step 3—ramp the humidity back down to 20% RH over 1.5 hours

Step 4—hold the sample at 20% RH for 0.5 hours

Step 5—repeat Steps 2 through 4, then stop

The following three data points were used as an indicator of powder response to humidity exposure: (i) maximum percent weight gain (i.e., water gain) during the first ramp to 90% RH (DVS%1), (ii) % weight gain/loss at the end of the hold step between ramps (i.e. at the end of Step 4) (DVS%2), and (iii) maximum percent weight gain (i.e., water gain) during the second ramp to 90% RH (DVS%3). The maximum percent weight gain during the first ramp to 90% RH (DVS%1) was used as an indicator of relative powder hygroscopicity. Differences between DVS%1 and DVS%3 were used as an indicator of irreversible changes occurring in the powder as a result of exposure to high humidities.

The range of water uptake was quite broad. Water uptake values for the various formulations ranged from about 1% water uptake at the test limit up to about 20% water uptake. Class I formulations showed the highest water uptake. Several formulations, including many formulations of Class I, showed significant hysteresis upon repeated humidity cycling. The majority of formulations, including most of Classes II, IV, VII, and VIII and all of Classes III, V, and VI, however, showed little or no hysteresis effect.

Table V shows several formulations exhibiting acceptable water uptake characteristics. Each of these formulations had low initial water uptake (DVS%1) and showed little or no hysteresis effect upon repeated humidity cycling. The test indicates that it is possible to produce a large porous particle with salmeterol and ipratropium bromide that will have very little tendency to absorb moisture when exposed to humidity.

TABLE V

Formulations Exhibiting Acceptable Water Uptake Characteristics

| Formulation | Class | Composition | DVS % 1 | DVS % 2 | DVS % 3 |
|---|---|---|---|---|---|
| A | III | DPPC/DSPC/Leucine/IB/SX | 4.2 | 0.0 | 4.1 |
| B | V | DPPC/DSPG/Leucine/IB/SX | 7.1 | 0.0 | 7.1 |
| C | VII | Leucine/IB/SX | 1.9 | 0.0 | 1.9 |
| D | VII | Leucine/Mannitol/IB/SX | 2.1 | 0.0 | 2.1 |
| E | IV | MSPC/DMPE/Leucine/IB/SX | 3.9 | −0.1 | 3.6 |
| F | II | DMPE/Leucine/IB/SX | 2.7 | 0.0 | 2.6 |
| G | IV | MSPC/DSPC/Leucine/IB/SX | 7.6 | 0.1 | 7.4 |
| H | VIII | Leucine/Maltodextrin/DMPE/IB/SX | 4.7 | 0.3 | 4.5 |
| I | V | DPPE/DSPG/Leucine/IB/SX | 6.0 | 0.0 | 6.0 |
| J | III | DSPC/Leucine/IB/SX | 7.5 | 0.0 | 7.4 |
| K | II | DPPE/DMPE/Leucine/IB/SX | 3.3 | −0.2 | 3.1 |

SX = salmeterol xinafoate; IB = ipratropium bromide

Particles containing the same components and lipid proportions as Formulation A, exhibited decreasing water uptake as phospholipid content was reduced and amino acid concentration was increased. In general, particles of Classes VII and VIII showed lower water uptake as compared to the formulations containing moderate to high levels of traditional phospholipids such as DPPC or DSPC.

DVS scan results for Formulations A through E are shown in FIGS. 5 through 8.

b) Differential Scanning Calorimetry

Differential scanning calorimetry was employed to monitor thermal events during temperature ramping of particles for most of the dry powder formulations. DSC studies were performed to gain insight into the thermal properties of the matrices that were used for different groups of formulations.

DSC was performed using a Series 2920 Differential Scanning Calorimeter (TA Instruments, New Castle Del.). Indium metal was used as the calibration standard. Samples for DSC were hermetically sealed in aluminum DSC pans. For all scans, the samples were equilibrated at 25° C., held isothermally for 1 min, and heated at rate of 100° C./min to a final temperature of 100° C. The transition temperature, $T_m$, was determined to be the temperature at the signal maximum for a change in heat flow.

Table VI shows the transition temperature, $T_m$, for the particles of each of the formulation classes that exhibited phase transitions. Note that most Class VII and VIII formulations did not exhibit phase transitions over the temperature range analyzed. Table VII shows transition temperature for some of the particle formulations evaluated. As shown in Table VII, all of Formulations A to K, exhibiting phase transitions over the temperature range examined, had transition temperatures above 50° C., with most above 60° C.

TABLE VI

DSC Transition Temperature Ranges by Formulation Class

| Class | Transition Temperature (° C.) | |
|---|---|---|
| | Low | High |
| I | 56.03 | 63.78 |
| II | 44.47 | 85.91 |
| III | 48.05 | 69.46 |
| IV | 54.94 | 79.02 |

TABLE VI-continued

DSC Transition Temperature Ranges by Formulation Class

| Class | Transition Temperature (° C.) | |
|---|---|---|
| | Low | High |
| V | 65.27 | 77.52 |
| VI | 61.36 | 84.81 |

TABLE VII

Formulations Exhibiting Acceptable Thermal Properties

| Formulation | Class | Composition | Transition Temperature (° C.) |
|---|---|---|---|
| A | III | DPPC/DSPC/Leucine/IB/SX | 64.35 |
| B | V | DPPC/DSPG/Leucine/IB/SX | 77.31 |
| C | VII | Leucine/IB/SX | No Transitions (25-100° C.) |
| D | VII | Leucine/Mannitol/IB/SX | No Transitions (25-100° C.) |
| E | IV | MSPC/DMPE/Leucine/IB/SX | 79.02 |
| F | II | DMPE/Leucine/IB/SX | 81.32 |
| G | IV | MSPC/DSPC/Leucine/IB/SX | 56.96 |
| H | VIII | Leucine/Maltodextrin/DMPE/IB/SX | No Transitions (25-100° C.) |
| I | V | DPPE/DSPG/Leucine/IB/SX | 77.52 |

TABLE VII-continued

Formulations Exhibiting Acceptable Thermal Properties

| Formulation | Class | Composition | Transition Temperature (° C.) |
|---|---|---|---|
| J | III | DSPC/Leucine/IB/SX | 65.40 |
| K | II | DPPE/DMPE/Leucine/IB/SX | 82.30 |

SX = salmeterol xinafoate;
IB = ipratropium bromide

EXAMPLE 9

The particle formulations of Tables I and III were evaluated for ability to resist physical changes in the Second Tier of testing. Powder formulations were evaluated in terms of fine particle fractions after thermal stress testing. Ten milligrams of each powder formulation was deposited into size 2 HPMC capsules. These filled capsules were then placed in desiccated bags and into a low-humidity, approximately 15% relative humidity, oven at 45° C. or 55° C. for six hours. After the six hours of heat stressing, the capsules were brought into a humidity controlled room, approximately 30% relative humidity, where the particles were allowed to cool to ambient temperature over about one-half hour. Then fine particle fractions were measured using a two-stage ACI as described in Example 7(c). Fine particle fraction was measured three times for each formulation held at each temperature (i.e., 45° C. or 55° C.) and also for particles held at room temperature.

Tables VIII and 1×show the average fine particle fractions (FPF) measured following thermal stress testing and their relative standard deviations (RSD). Tables VII and VIII show FPF(<5.6) and FPF(<3.4), respectively, for particles held at room temperature, 45° C. and 55° C. for a period of six hours.

TABLE VIII

Fine Particle Fraction (FPF) Less than 5.6 Microns

| Formulation | $T_{room}$ FPF (<5.6 μm) (RSD) | 45° C. FPF (<5.6 μm) (RSD) | 55° C. FPF (<5.6 μm) (RSD) |
|---|---|---|---|
| A | 0.618 (1.6%) | 0.574 (9.94%) | 0.710 (1.5%) |
| B | 0.504 (3.2%) | 0.507 (1.23%) | 0.400 (5.26%) |
| C | 0.504 (7.6%) | 0.552 (6.63%) | 0.602 (3.8%) |
| D | 0.667 (10.96%) | 0.707 (5.92%) | 0.684 (1.3%) |
| E | 0.567 (4.1%) | 0.589 (4.26%) | 0.502 (1.27%) |
| F | 0.478 (7.6%) | 0.499 (1.15%) | 0.456 (4.0%) |
| G | 0.632 (5.83%) | 0.526 (1.22%) | 0.645 (5.5%) |
| H | 0.460 (11.3%) | 0.603 (5.0%) | 0.544 (11.1%) |
| I | 0.539 (2.80%) | 0.477 (2.18%) | 0.294 (4.06%) |
| J | 0.588 (2.8%) | 0.457 (8.8%) | 0.200 (n = 1) |
| K | 0.432 (11.5%) | 0.518 (5.1%) | 0.473 (4.22%) |

TABLE IX

Fine Particle Fraction (FPF) Less than 3.4 Microns

| Formulation | $T_{room}$ FPF (<3.4 μm) (RSD) | 45° C. FPF (<3.4 μm) (RSD) | 55° C. FPF (<3.4 μm) (RSD) |
|---|---|---|---|
| A | 0.227 (3.1%) | 0.203 (13.4%) | 0.265 (13.8%) |
| B | 0.189 (7.9%) | 0.170 (8.58%) | 0.142 (0.034%) |
| C | 0.256 (15.9%) | 0.240 (13.4%) | 0.291 (15.8%) |
| D | 0.363 (17.6%) | 0.400 (2.74%) | 0.368 (4.4%) |
| E | 0.240 (3.7%) | 0.243 (8.34%) | 0.203 (3.44%) |
| F | 0.213 (5.7%) | 0.175 (0.559%) | 0.210 (3.9%) |
| G | 0.329 (8.05%) | 0.209 (4.36%) | 0.269 (5.9%) |
| H | 0.181 (7.46%) | 0.276 (9.1%) | 0.232 (7.2%) |
| I | 0.229 (4.5%) | 0.189 (1.58%) | 0.121 (12.53%) |
| J | 0.282 (5.7%) | 0.227 (7.9%) | 0.140 (n = 1) |
| K | 0.156 (17.0%) | 0.190 (8.2%) | 0.175 (4.20%) |

Formulations I and J did not emit fully from the capsules after heat stressing at 55° C. These formulations essentially failed the heat stress testing criteria since their respective fine particle fraction dropped after thermal stressing. All other formulations after thermal stressing performed similarly to particles kept at room temperature although some fine particle fractions increased or decreased slightly after heat stressing. It is believed that some FPF's were increased following heat stressing due to removal of trace amounts of water via heating.

The results of this test indicates that the selection of excipients can have an impact on the ability of a formulation to withstand elevated temperatures without effecting the aerosol characteristics.

EXAMPLE 10

Particles were also tested in the Second Tier for protection from bronchoconstriction following a bronchoprovocative metbacoline challenge in a guinea pig model of airway hyperresponsiveness. Several powders containing ipratropiulm bromide and salmeterol xinafoate and produced as in Example 6 were selected for in-vivo evaluation. The bronchoprotection provided by the Example 6 powders was compared to that of a control aerodynamically light placebo and also to that of Serevent® Dry Powder blended with micronized lactose. Bronchoprotection was assessed at a single timepoint, 12 hours post-treatment.

Dry powder formulations and control treatments were delivered to anesthetized animals by intratracheal insufflation. Salmeterol xinafoate alone or ipratropium bromide and salmeterol xinafoate in combination, for use in the in vivo studies, were delivered via insufflation at a nominal dose of 1 μg active drug. To facilitate dosing through the insufflation device, powders to be tested were blended with an aerodynamically light placebo powder for a total delivery mass of 2 mg. Aerodynamically light placebo particles consisting of 35% DPPC, 35% DSPC, and 30% leucine were prepared by spray drying through methods similar to those of Example 6. All bulk powders were stored in a dry room with controlled temperature and humidity (70° F., 30% R.H.) prior to weighing. Each of the blended test doses were weighed into size 2 HPMC individual capsules stored desiccated until administration when the powders were transferred from the capsule into the insufflation device for dosing.

A nominal dose of 1 μg of salmeterol in a commercially available dry powder form (0.4% load of salmeterol) was insufflated in guinea pigs as a positive control. The positive control was obtained directly from powder-containing blisters inside a Serevent® Dry Powder inhalation aerosol device stored at room temperature. The salmeterol/lactose dry powder (0.4% load of salmeterol) was blended with micronized lactose placebo powder to achieve a 1 μg nominal dose of salmeterol. Two milligrams of this blend was weighed into size 2 HPMC individual capsules stored desiccated until administration when the powders were transferred from the capsule into the insufflation device for dosing.

Young adult male Hartley guinea pigs were obtained from ElmHill Breeding Laboratories, Inc. (Chemsford, Mass.). At the time of use, the animals weighed between 314 and 413 g (mean weight was 356 g±2.6 g (S.E.M.)).

The powder was delivered to the lungs of anesthetized animals by an insufflation technique using a Penn-Century insufflation device (Philadelphia, Pa.). Animals were randomly selected from the test population for each treatment. Using a laryngoscope, the delivery tube of the insufflator was inserted through the oropharynx and into the trachea until the tip of the tube was about a centimeter from the carina (first bifurcation). A 3 mL bolus was used to activate the Penn-Century devices and deliver the powder from the dosing barrel. This bolus of air was repeated three times for a total of three discharges per powder dose in order to decrease or eliminate powder residues in the sample chamber. Animals were then returned to their cages and observed until recovery from anesthesia; subsequently bronchoprotection was assessed.

A BUXCO Unrestrained Whole-Body Plethysmography System (BUXCO Electronics, Inc., Sharon, Conn.) was used with customized software to assess pulmonary function changes. Airway hyperresponsiveness in normal animals to nebulized methacholine (750 µg/mL solubilized in saline; Sigma Chemical Company, St. Louis, Mo.) was assessed using the BUXCO system both prior to dosing (i.e., as an assessment of baseline airway hyperresponsiveness) and at 12 hours following particle administration. The enhanced pause value (PenH), a flow-based indicator of airway resistance, was used as an indicator of bronchoprotection. A significant increase in this value indicated significant bronchoconstriction, while prevention of this increase in response to methacholine indicated bronchoprotection.

Figure 9:
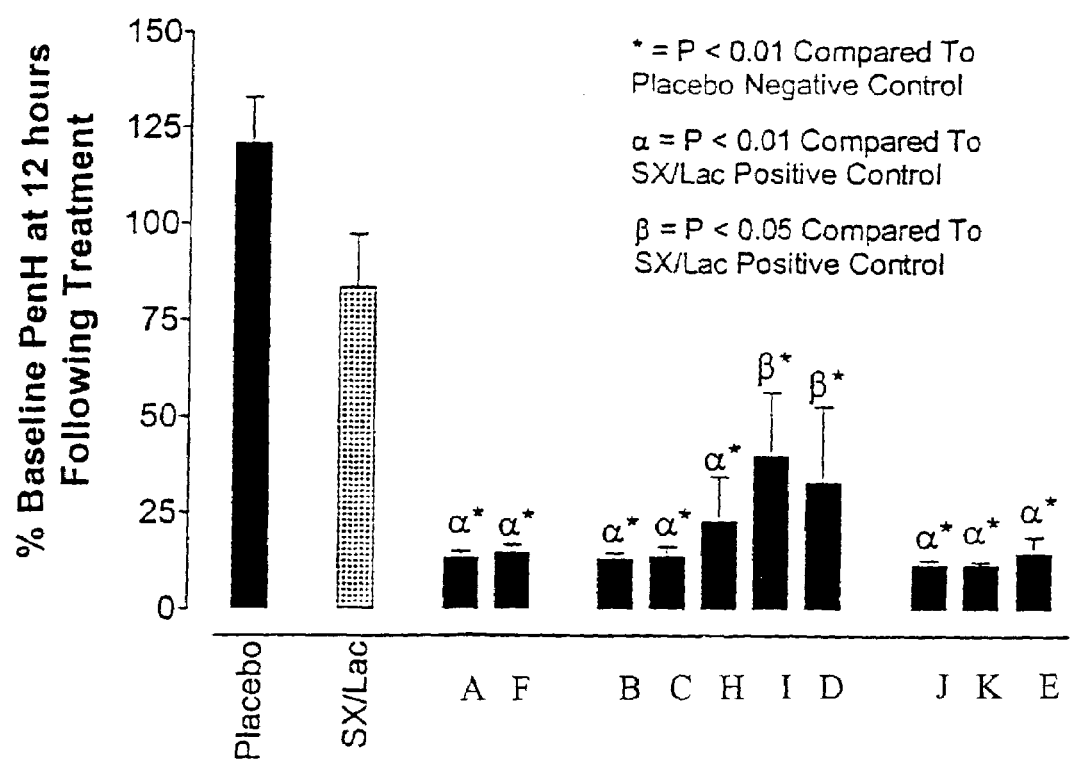

FIG. 9 shows the results of the 12 hour study as percentage of baseline enhanced pause (PenH) at 12 hours after particle administration to the animal subjects (n=6 to 8 per group). Statistical significance (P) is indicated for each test powder.

EXAMPLE 11

Particle formulations were evaluated for solid state stability in the Third Tier of testing. X-Ray Diffraction (XRD) was performed on formulations before and after 24 hour exposure to 75% Relative Humidity. XRD was performed in the range of 2-50° C. at 1° C./min under $N_2$ purge. Most formulations tested exhibited little or no change in crystallinity after exposure. Formulation E, however, showed a small percent change in the scattering results after extended exposure to elevated humidity, likely due to recrystallization of amorphous drug content.

EXAMPLE 12

In Tier 3 testing, particle formulations produced as in Example 6 were subjected to a multiple timepoint study of bronchoprotection in a guinea pig model of airway hyperresponsiveness. Several particle formulations examined in the single timepoint 12 hour study (Example 10) were selected for evaluation in a more extensive, multi-point study that looked at the animal response out to and beyond 2 hours. The methods of powder preparation and administration were the same as in Example 10. Test animals were randomly selected for treatment and divided into eight test groups. Pulmonary function testing following treatment with the dry powder formulations occurred at multiple timepoints which included 2, 12, 16, 20, 24, 48 and 72 hours following treatment.

Figure 10:
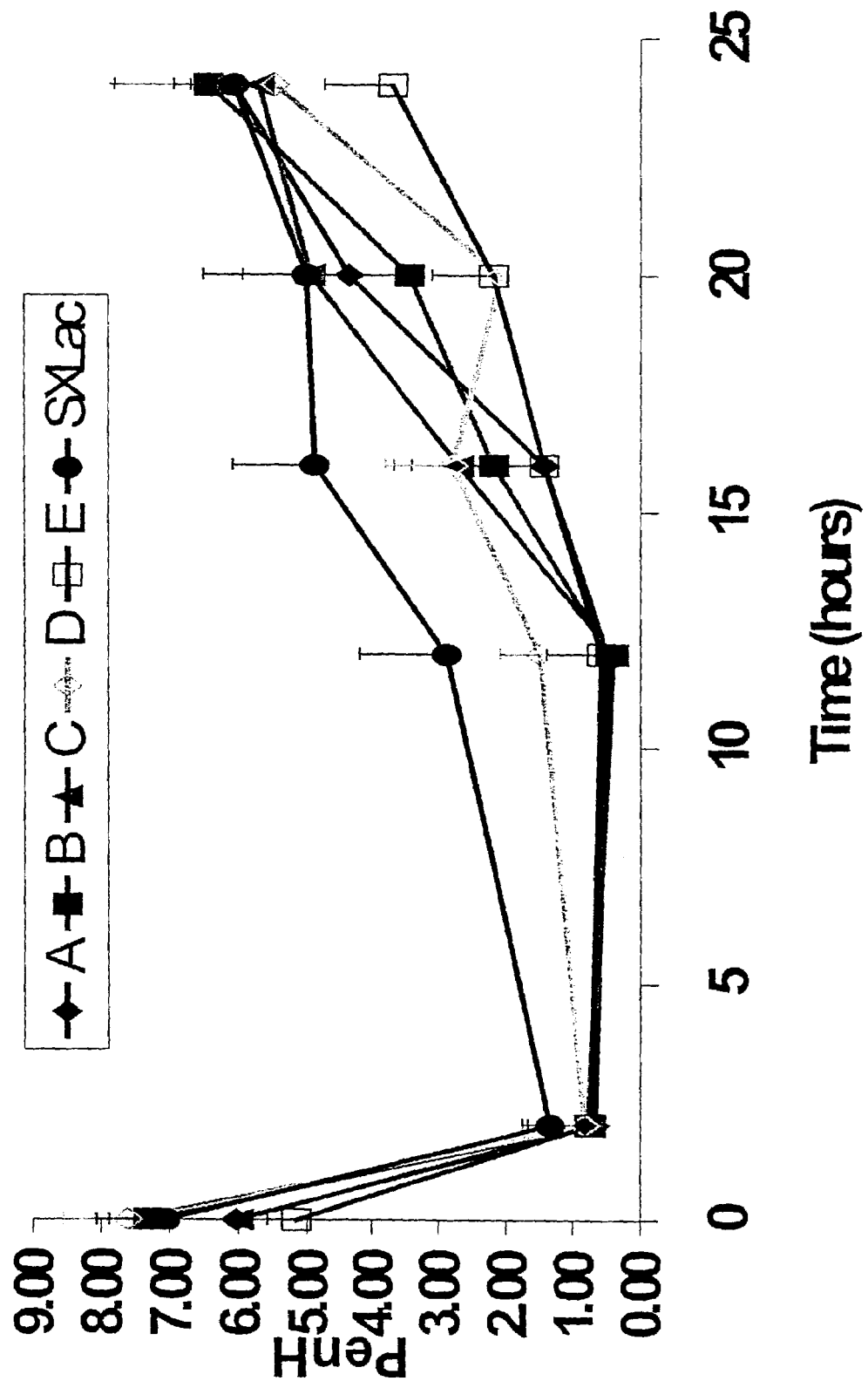
Figure 11:
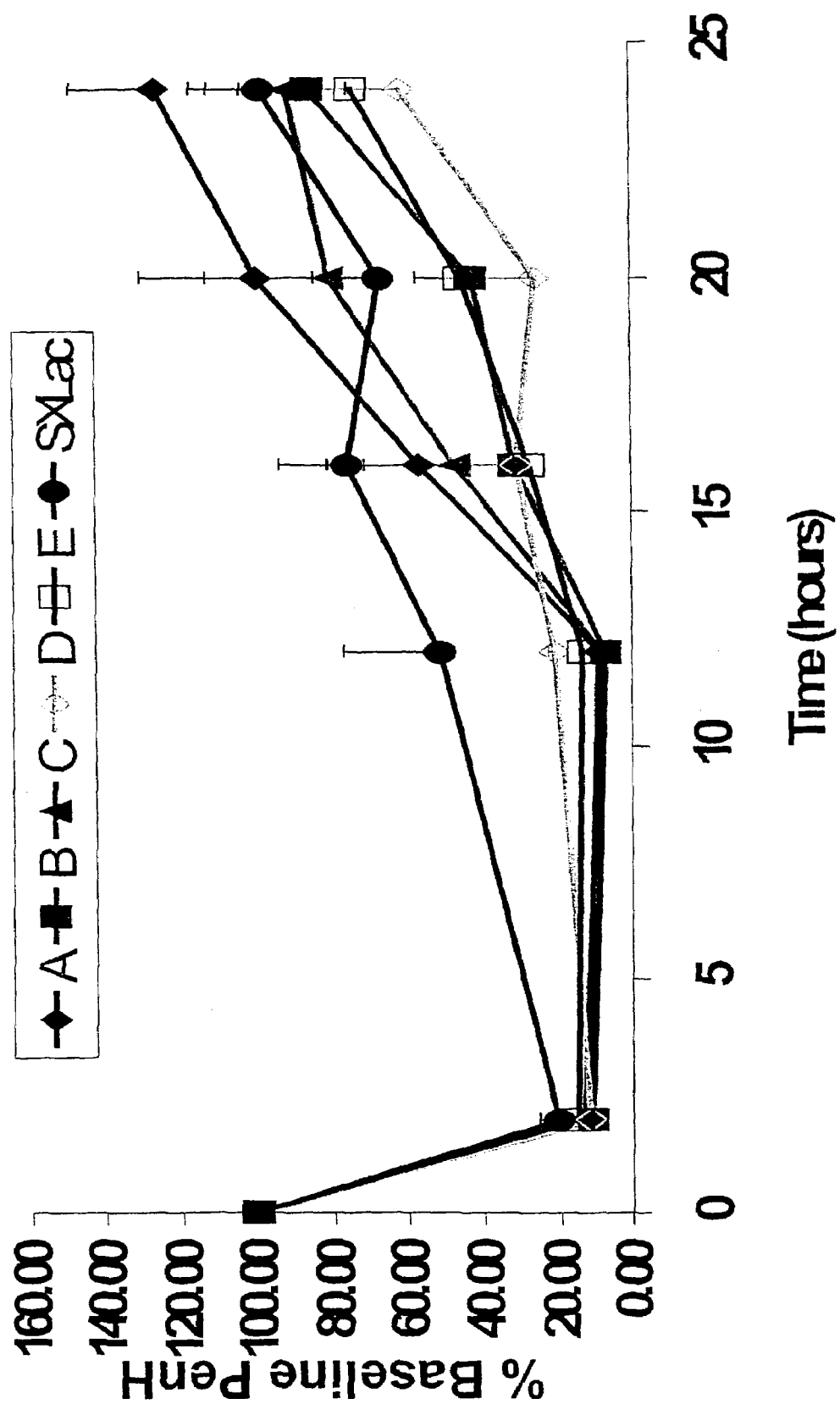

Graphs of compiled PenH and % of PenH over time are found in FIGS. 10 and 11. All formulations exhibited significantly greater bronchoprotection through at least 12 hours when compared to the salmeterol/lactose positive control. In addition, Formulations B, D and E exhibited significantly greater bronchoprotection through at least 16 hours when compared to the control.

While this invention has been particularly shown and described with references to preferred embodiments thereof, it will be understood by those skilled in the art that various changes in form and details may be made therein without departing from the scope of the invention encompassed by the appended claims.

What is claimed is:

1. Non-polymeric particles for pulmonary delivery of trospium via a dry powder inhaler, the particles consisting of:
   a. trospium;
   b. leucine, wherein leucine is present in the particles in an amount between 75 and 85% by weight,
   c. optional buffer or salt; and
   d. optional sugar
   said particles having a tap density of less than about 0.4 $g/cm^3$.

2. The particles of claim 1 wherein the particles have a tap density less than or equal to about 0.1 $g/cm^3$.

3. The particles of claim 1 wherein the particles have a mean geometric diameter of about 5 to 30 microns.

4. The particles of claim 1 wherein the particles have a mean geometric diameter of about 9 to 30 microns.

5. The particles of claim 1 wherein the particles have an aerodynamic diameter of about 1 to 5 microns.

6. The particles of claim 1 wherein the particles comprise about 5 to 10 weight percent of trospium.

7. The particles of claim 1 wherein the particles comprise about 8 weight percent of trospium.

8. The particles of claim 1 wherein the particles are for the sustained release of trospium.

9. A method comprising delivering via the pulmonary system to a patient in need of treatment, an effective amount of the particles of claim 1.

10. A method for pulmonary delivery of trospium via a dry powder inhaler, the method comprising administering particles consisting of:
    a. trospium;
    b. leucine, wherein leucine is present in the particles in an amount between 75 and 85% by weight,
    c. optional buffer or salt; and
    d. optional sugar
    said particles having a tap density of less than about 0.4 $g/cm^3$.

11. The method of claim 10 wherein the particles have a tap density less than or equal to about 0.1 $g/cm^3$.

12. The method of claim 10 wherein the particles have a mean geometric diameter of about 5 to 30 microns.

13. The method of claim 10 wherein the particles have a mean geometric diameter of about 9 to 30 microns.

14. The method of claim 10 wherein the particles have an aerodynamic diameter of about 1 to 5 microns.

15. The method of claim 10 wherein the particles comprise about 5 to 10 weight percent of trospium.

16. The method of claim 10 wherein the particles comprise about 8 weight percent of trospium.

17. The particles of claim 1, wherein the leucine is present in an amount of about 81% by weight.

18. The particles of claim 17 further comprising a buffer.

19. The particles of claim 1, wherein the particles are spray dried.

20. The method of claim 10, wherein the leucine is present in an amount about 81% by weight.

21. The method of claim 20 further comprising a buffer.

22. The method of claim 10, wherein the particles are spray dried.

* * * * *